(12) United States Patent
Urabe et al.

(10) Patent No.: US 8,265,373 B2
(45) Date of Patent: Sep. 11, 2012

(54) METHOD AND APPARATUS FOR INSPECTING APPEARANCE OF LONG-LENGTH OBJECTS

(75) Inventors: Kouji Urabe, Kanagawa (JP); Tatsuji Kaneko, Kanagawa (JP); Hirotaroh Tada, Kanagawa (JP); Haruyoshi Toyoda, Shizuoka (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 327 days.

(21) Appl. No.: 12/664,731

(22) PCT Filed: Jun. 13, 2008

(86) PCT No.: PCT/JP2008/060876
§ 371 (c)(1),
(2), (4) Date: May 14, 2010

(87) PCT Pub. No.: WO2008/153141
PCT Pub. Date: Dec. 18, 2008

(65) Prior Publication Data
US 2011/0052039 A1   Mar. 3, 2011

(30) Foreign Application Priority Data

| Jun. 15, 2007 | (JP) | 2007-159131 |
| Jun. 15, 2007 | (JP) | 2007-159145 |
| Jun. 15, 2007 | (JP) | 2007-159157 |
| Jun. 15, 2007 | (JP) | 2007-159162 |

(51) Int. Cl.
*G06K 9/00* (2006.01)
(52) U.S. Cl. .................................................. 382/141
(58) Field of Classification Search .................... None
See application file for complete search history.

(56) References Cited

U.S. PATENT DOCUMENTS

| 4,801,207 A | 1/1989 | Williams |
| 5,408,104 A * | 4/1995 | Gorria et al. ............ 250/559.04 |

FOREIGN PATENT DOCUMENTS

| JP | 62-503121 | 12/1987 |
| JP | 2-226003 A | 9/1990 |
| JP | 6-241740 A | 9/1994 |
| JP | 7-260444 A | 10/1995 |
| JP | 10-264174 A | 10/1998 |
| JP | 2003-057020 A | 2/2003 |
| JP | 2003-172611 A | 6/2003 |
| JP | 2004-198374 A | 7/2004 |
| JP | 2007-003243 A | 1/2007 |

* cited by examiner

*Primary Examiner* — Paul Danneman
(74) *Attorney, Agent, or Firm* — Carrier Blackman & Associates, P.C.; Joseph P. Carrier; William D. Blackman

(57) ABSTRACT

An apparatus for inspecting appearance of long-length object takes images of lighted line every predetermined timing while making the hose move in the long-length direction. By this, the contours of the hose are taken continuously and correctly over the length direction of the hose. The height direction position data of the lighted line corresponding to each of the width direction position of the hose are extracted, and the height direction position data are subtracted by the base data provided so as to correspond to each of the width direction position. Thus, the arc shape of the outer surface of the hose is canceled from the height direction position data. Also, the height direction position data of each taken image which are given the subtracting is put in image-taking order, and an inspection image is made on the basis of the predetermined color.

14 Claims, 15 Drawing Sheets

THE POSITION OF THE IMAGE DATA OF FIG. 11

| | t1 | t2 | t3 | t4 | t5 | t6 | t7 | t8 | t9 | t10 | | Av6 | Av7 |
|---|---|---|---|---|---|---|---|---|---|---|---|---|---|
| X15 | | | | | | 68.2 | | | | | | 68.2 | 68.3 |
| X16 | | | | | | 70.5 | | | | | | 70.5 | 70.7 |
| X17 | | | | | | 72.0 | | | | | ... | 72.0 | 72.1 |
| X18 | | | | | | 73.4 | | | | | | 73.4 | 73.5 |
| X19 | | | | | | 74.5 | | | | | | 74.5 | 74.7 |

IMAGE TAKING ORDER

IMAGE TAKING ORDER

IMAGE TAKING ORDER

IMAGE TAKING ORDER

METHOD AND APPARATUS FOR INSPECTING APPEARANCE OF LONG-LENGTH OBJECTS

TECHNICAL FIELD

The present invention relates to, for example, a method for inspecting appearance of a long-length object and an apparatus thereof for inspecting appearance of a long-length hose or an electric wire which is formed by vulcanizing in a state in which a cloth member wraps spirally on an outer surface of the long-length object and the cloth member being removed from the outer surface after vulcanization.

BACKGROUND ART

Generally, there are known a hose formed by vulcanizing in a state in which a resin covers an outer surface and the resin being removed after vulcanization, and a hose formed by vulcanizing in a state in which a cloth member wraps spirally an outer surface, and the cloth member being removed after vulcanization.

In addition, there is known a method for inspecting appearance of a long-length object which includes the steps of using, for example, an image taking device which can take images of an outer surface of a long-length hose continuously, taking images of an outer surface of a long-length hose continuously with the image taking when the long-length hose is moving in a length direction, and judging existence of unevenness, a defect, and the like on an outer surface of the hose on taken images.
Patent Document 1: Japanese Patent publication H10-264174
Patent Document 2: Japanese Patent publication 2007-003243

DISCLOSURE OF THE INVENTION

Problem to be Solved by the Invention

On a hose which is formed by vulcanizing in a state in which its outer surface is covered with a resin, the outer surface of the hose is smooth and has a gloss. Hence, when the outer surface of the hose has unevenness or a defect, reflection of light in a portion of the unevenness or defect is characteristic. By this, the existence of the unevenness or defect can be judged by the above-mentioned appearance inspection method.

Nevertheless, in a hose which is formed by vulcanizing in a state in which a cloth member wraps spirally an outer surface, an outer surface of the hose becomes rough by remains of texture being transferred, and hence, spiral recessed portions or convex portions arise in portions where the cloth member overlaps. By this, the outer surface of the hose has the spiral recessed portions or convex portions and is non-gloss and rough. Thus, since concave or convex portions always arise on the outer surface by the spiral recessed portions or convex portions, it is difficult to judge only an unusual level of unevenness correctly at the time of taking images of the outer surface by the above-mentioned appearance inspection method.

Furthermore, in the above-mentioned appearance inspection method, when an outer surface of a hose has a marking of a product name in a color different from a color of the hose, reflection of light at the marking position is different from reflection of light at other portions of the hose. By this, when judging the existence of the unevenness or defect correctly, the marking of the product name and the like becomes a hindrance.

On the other hand, not depending on the above-mentioned appearance inspection method, an inspector is also able to perform an inspection by tactile feeling and visual observation. Nevertheless, accuracy of the inspection varies according to inspector's level of skill.

An object of the present invention is to provide a method for inspecting appearance of a long-length object and an apparatus thereof which can correctly conduct an appearance inspection of a long-length object which is formed by vulcanizing in a state in which a cloth member wraps spirally the outer surface thereof.

Means for Solving the Problem

The present invention is a method for inspecting appearance of a long-length object formed by vulcanizing in a state in which a cloth member wraps spirally an outer surface of the long-length object and the cloth member being removed from the outer surface after vulcanization, the method comprising the steps of irradiating a slit light onto the outer surface of the long-length object by a light source, moving the light source and the long-length object relatively in the length direction of the long-length object, and taking images of a lighted line, formed on the outer surface of the long-length object by irradiated slit light, from a direction forming an angle relative to a face of the slit light every predetermined timing, extracting a plurality of height direction position data of the lighted line from each taken image respectively so that each height direction position datum corresponds respectively to a plurality of width direction positions of the long-length object, subtracting a plurality of base data, which are provided so as to correspond respectively to said each width direction position, and which are provided according to a shape of the outer surface of the long-length object, from said height direction position data respectively, making an inspection image by arranging subtracted height direction position data of said taken images conformity to the order of taking images so as to conform to a predetermined color standard, and judging existence of unusual on the inspection image on the basis of a predetermined judging standard.

In addition, the present invention is an apparatus for inspecting appearance of a long-length object formed by vulcanizing in a state in which a cloth member wraps spirally an outer surface of the long-length object and the cloth member being removed from the outer surface after vulcanization, the apparatus comprising a light source for irradiating a slit light onto the outer surface of the long-length object, a move mechanism for moving the light source and the long-length object relatively in the length direction of the long-length object, an image taking device capable of taking images of a lighted line, formed on the outer surface of the long-length object by irradiated slit light, from a direction forming an angle relative to a face of the slit light every predetermined timing, a position data extracting means for extracting respective height direction position data of the lighted line, which corresponds to a plurality of width direction positions of the long-length object, with respect to every taken image taken by the image taking device, a subtracting means for subtracting base data, which are provided to each of the width direction position according to a shape of the outer surface of the long-length object, from each of the height direction position data, which correspond to each of the width direction position, an inspection image making means for making an inspection image by arranging subtracted height direction position data of each taken image in image-taking order so as to conform to a predetermined color standard, and a judging means for judging existence of unusual on the inspection image on the basis of a predetermined judging standard.

Thereby, since slit light is irradiated toward the outer surface of the long-length object, a lighted line which is formed by the slit light being radiated on the outer surface of the long-length object shows contour of the long-length object in the position correctly. In addition, since an image of the lighted line is taken from the direction of forming the predetermined angle with the face of the slit light, an image of the contour of the long-length object in the position of the lighted line is taken correctly. Furthermore, an image of the lighted line is taken every predetermined timing with moving the light source and long-length object relatively in the length direction of the long-length object. Hence, images of the contour of the long-length object are taken continuously and correctly over the length direction of the long-length object. In addition, each of height direction position data of the lighted line, which corresponds to each width direction position of the long-length object, is extracted from every taken image. Furthermore, base data, which is provided every width direction position according to a shape of the outer surface of the long-length object, is subtracted from the height direction position data respectively. For this reason, for example, when the long-length object has a round cross section and position data according to designed size of the long-length object is used as the base data, an arc shape of the outer surface of the long-length object is canceled from the height direction position data. That is, the height direction position data after subtracting shows clearly the unevenness, defect, and the like of the outer surface of a long-length object. Furthermore, the height direction position data of each taken image which are given the subtracting is put in image-taking order, an inspection image is made on the basis of the predetermined color standard, and the presence of the unusual on the inspection image is judged on the basis of the predetermined judging standard. Hence, in comparison with a case in which an inspection image is made without canceling the arc shape of the outer surface of the long-length object, the unevenness, defect, and the like in the outer surface of the long-length object become clear on the inspection image.

Effect of the Invention

Thus, according to the present invention, it is possible to take images of the contour of the long-length object over a length direction continuously and correctly, and it is also possible to clarify the unevenness, defect, and the like in the outer surface of the long-length object on the inspection image. Hence, it is possible to perform correctly the appearance inspection of the long-length object which is formed by vulcanizing in a state in which a cloth member wraps spirally the outer surface.

The above-mentioned objects, other objects, features, and benefits of the present invention will become clear by the following description and accompanying drawings.

DESCRIPTION OF SYMBOLS

10 . . . irradiation device, 20 . . . move mechanism, 21 . . . belt conveyer, 30 . . . first guide mechanism, 31 . . . first guide member, 33 . . . auxiliary guide mechanism, 40 . . . second guide mechanism, 41 . . . second guide member, 50 . . . image taking device, 60 . . . controller, 61 . . . display unit, 62 . . . operation section, H . . . hose, S . . . slit light, L . . . lighted line, SP . . . the spiral recessed portion, K . . . defect, P . . . pitch, γ . . . angle, D . . . foreign material.

BEST MODE FOR CARRYING OUT THE INVENTION

Figure 1:
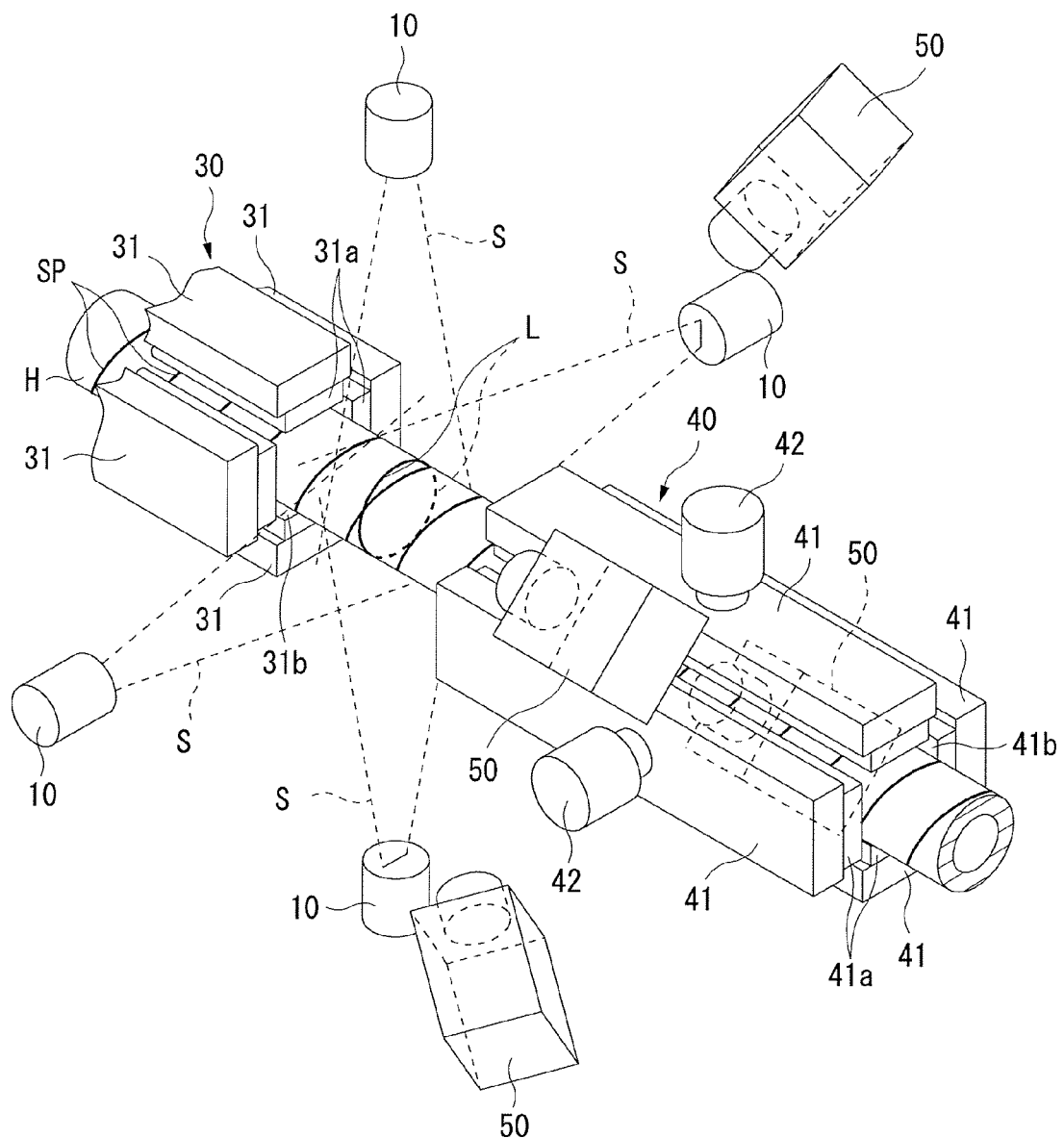
FIG. 1 is a perspective view of a principal part of an apparatus for inspecting appearance of a long-length object which shows a first embodiment of the present invention.
Figure 2:
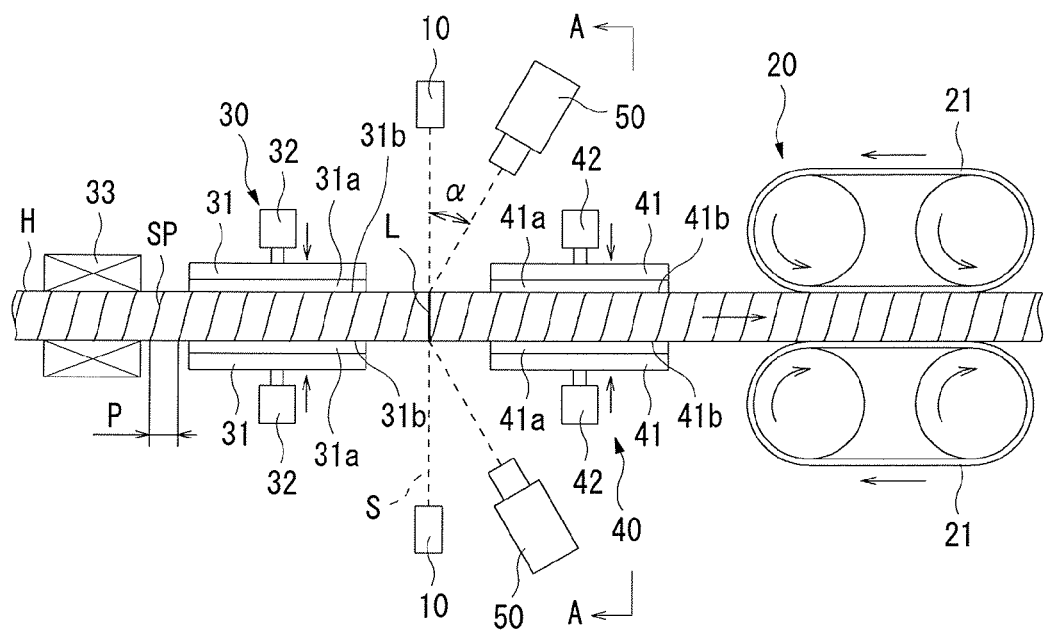
FIG. 2 is a side view of a principal part of the apparatus for inspecting appearance of a long-length object.
Figure 3:
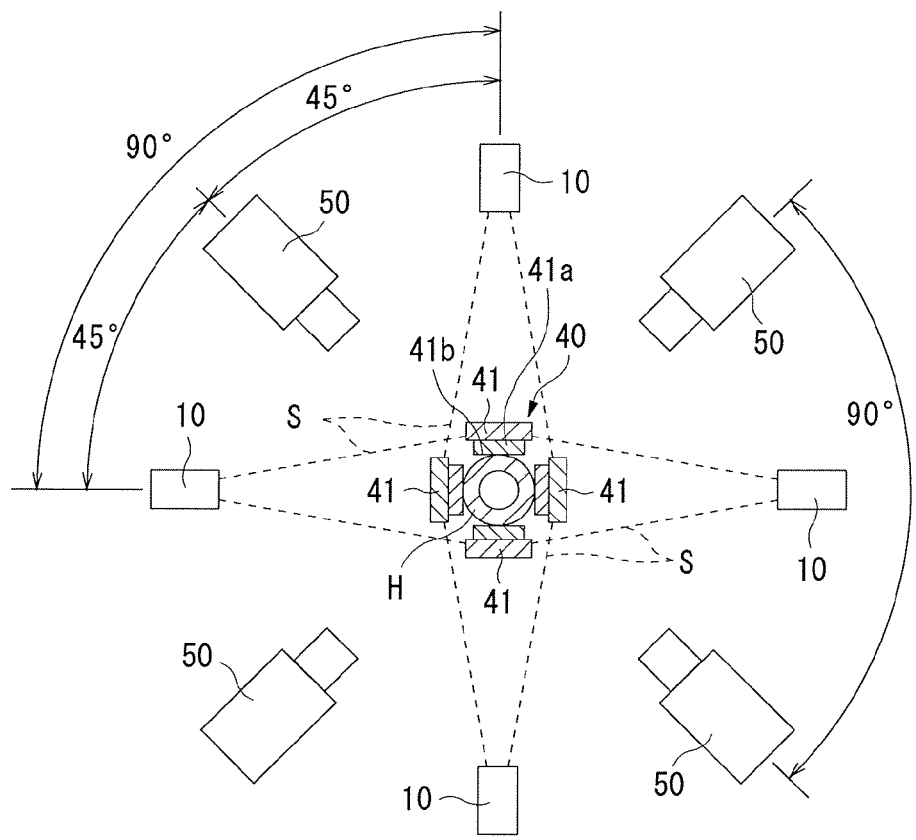
FIG. 3 is a sectional view taken on line A-A in FIG. 2.
Figure 4:
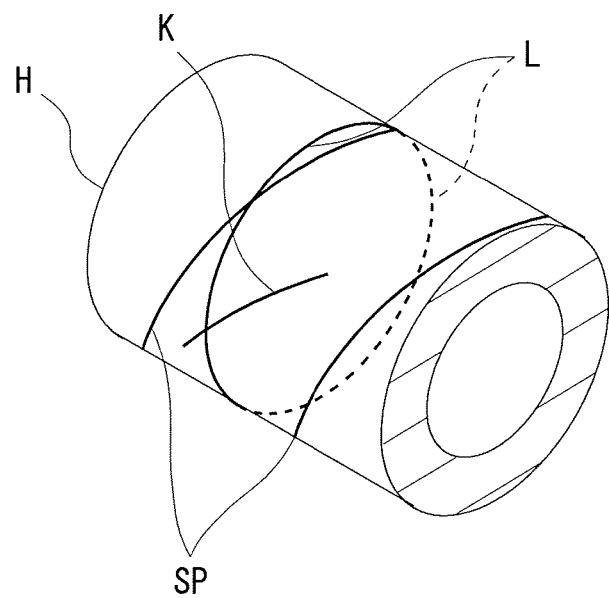
FIG. 4 is a perspective view of a principal part of a hose.
Figure 5:
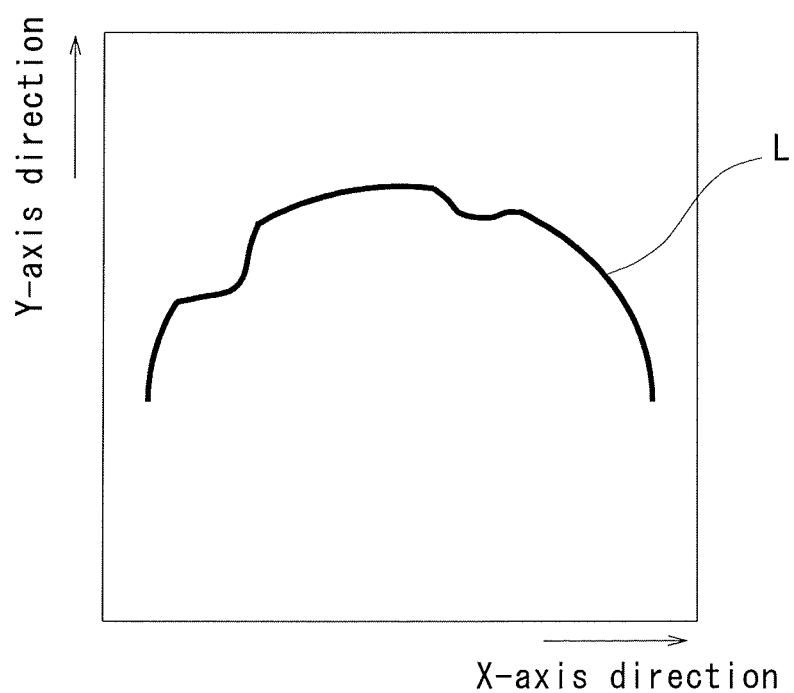
FIG. 5 is an example of a taken image.
Figure 6:
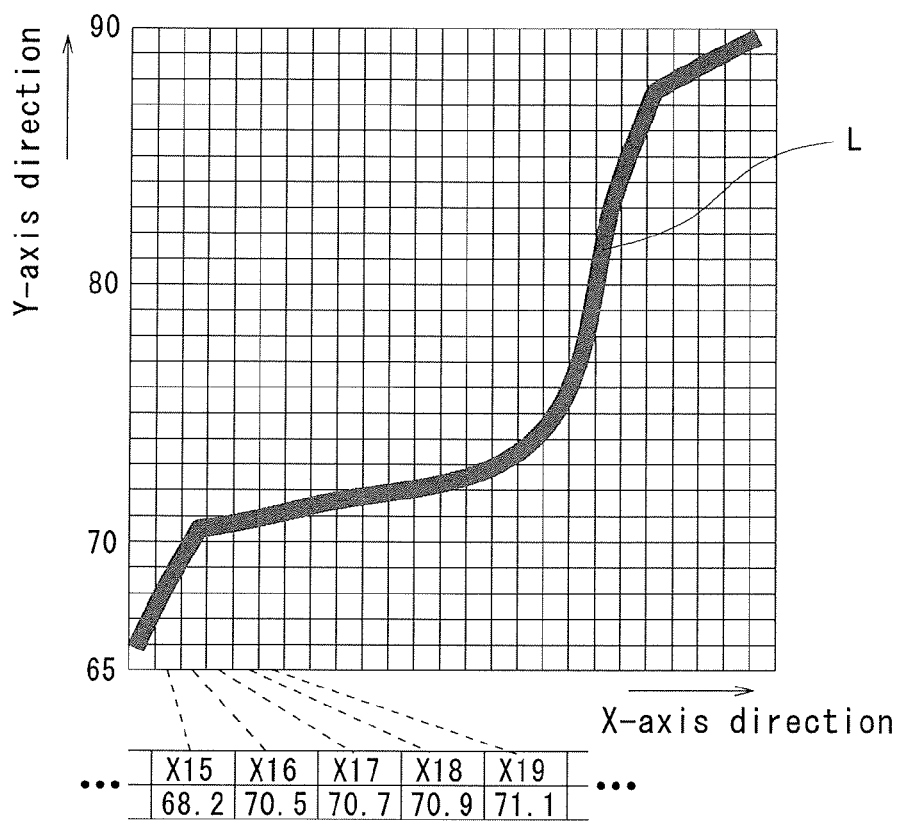
FIG. 6 is a partially enlarged view of FIG. 5.
Figure 7:
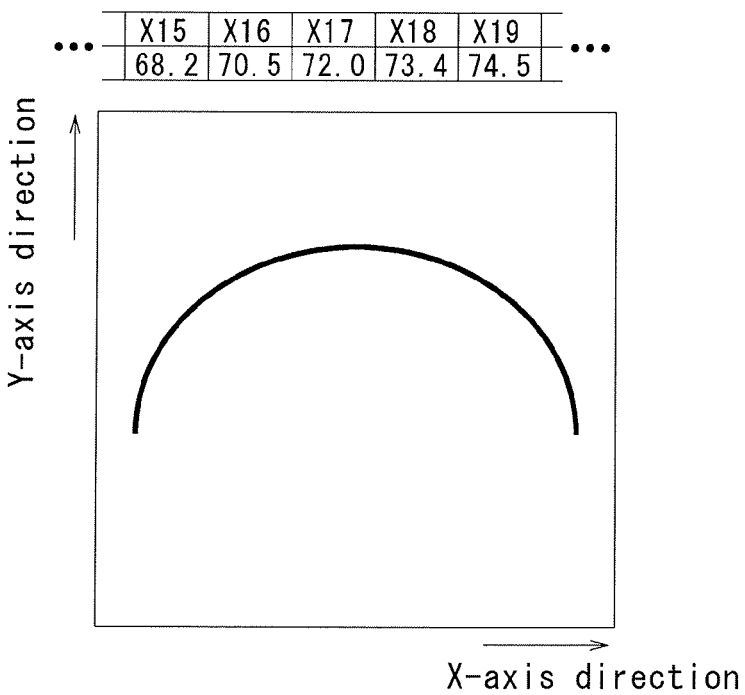
FIG. 7 is an example of base data.
Figure 8:
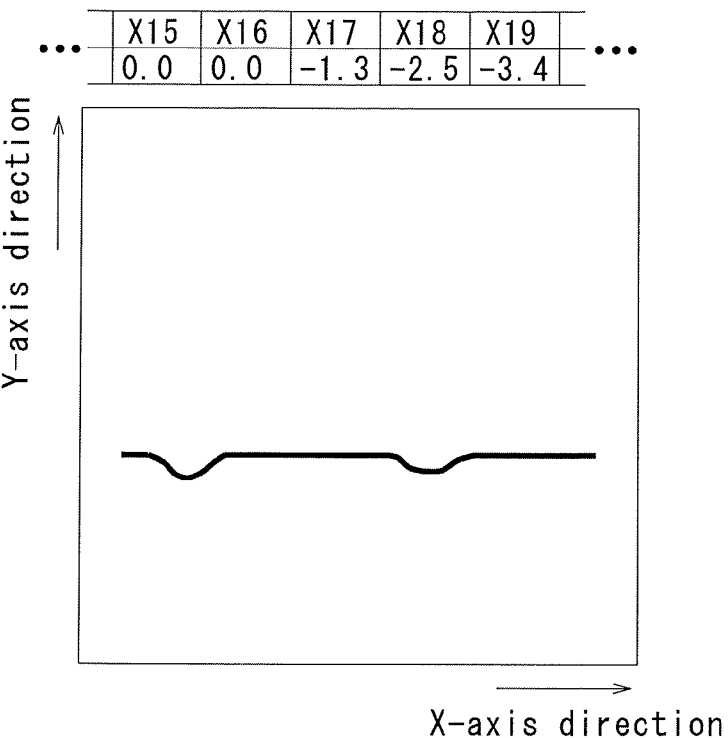
FIG. 8 is an example of height direction position data which is given subtracting.
Figure 9:
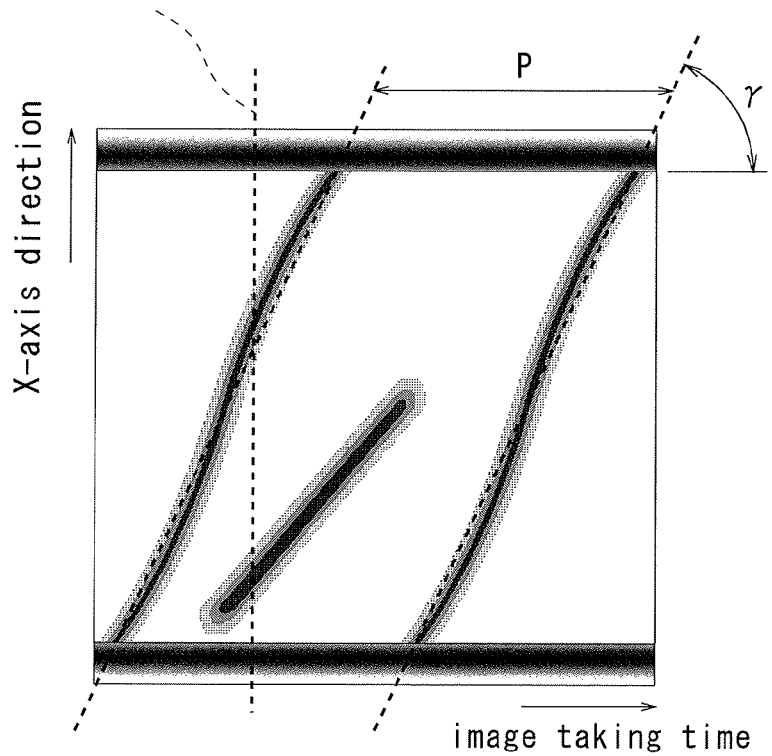
FIG. 9 is an example of an inspection image.
Figure 10:
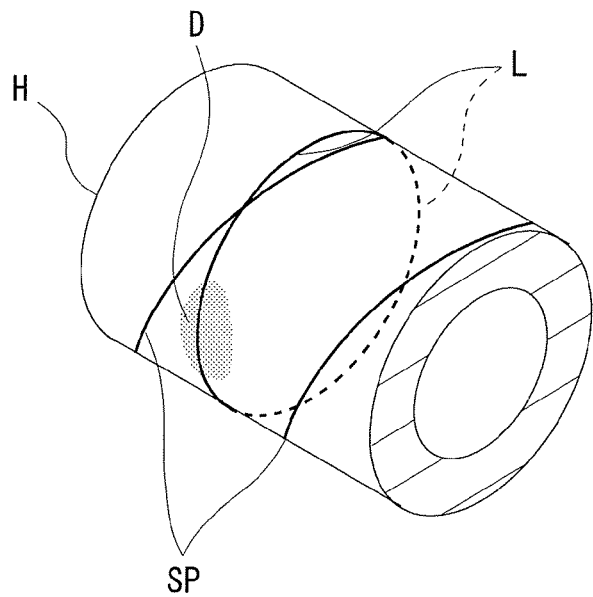
FIG. 10 is a perspective view of a principal part of a hose.
Figure 11:
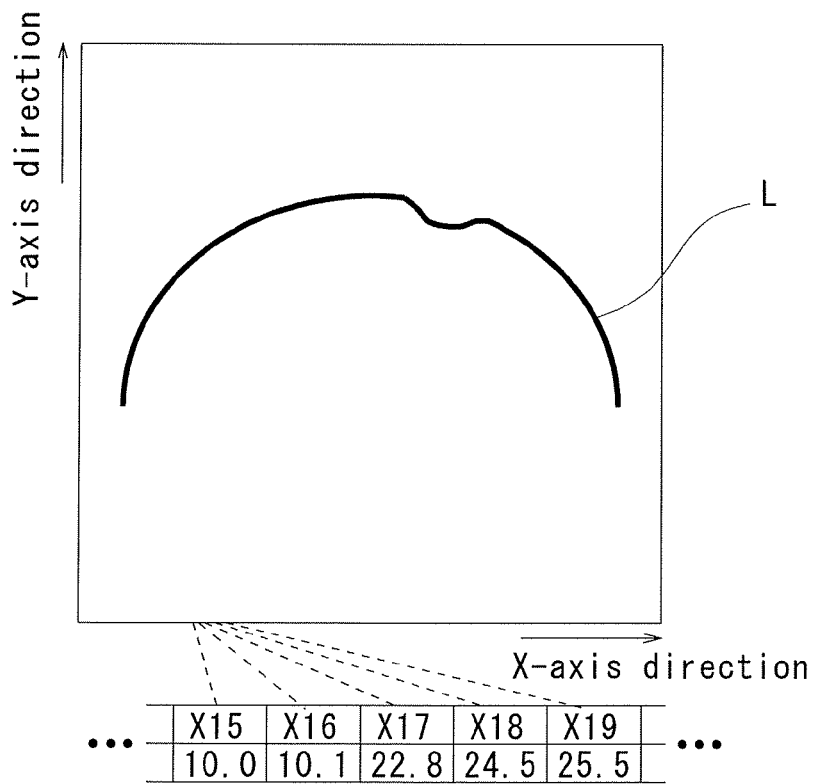
FIG. 11 is an example of a taken image.
Figure 12:
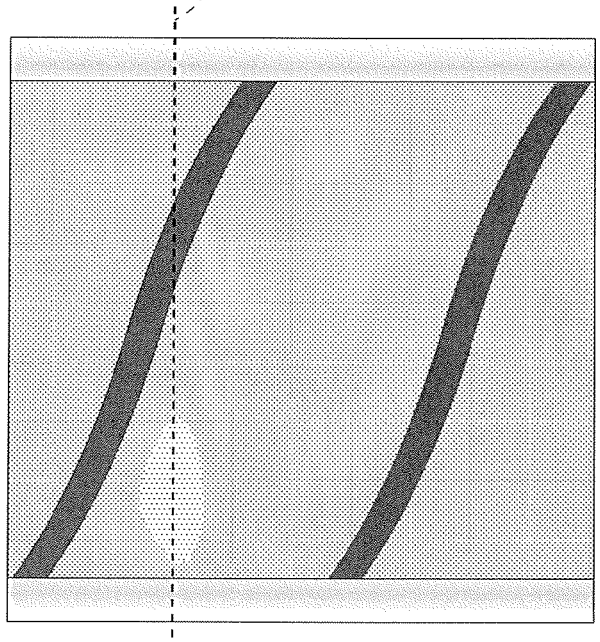
FIG. 12 is an example of a brightness inspection image.
Figure 13:
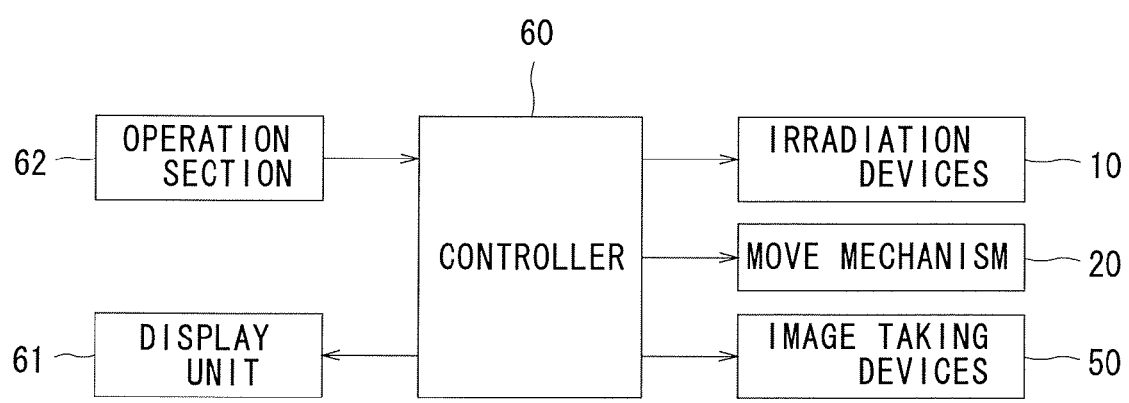
FIG. 13 is a block diagram of the apparatus for inspecting appearance of a long-length object.
Figure 14:
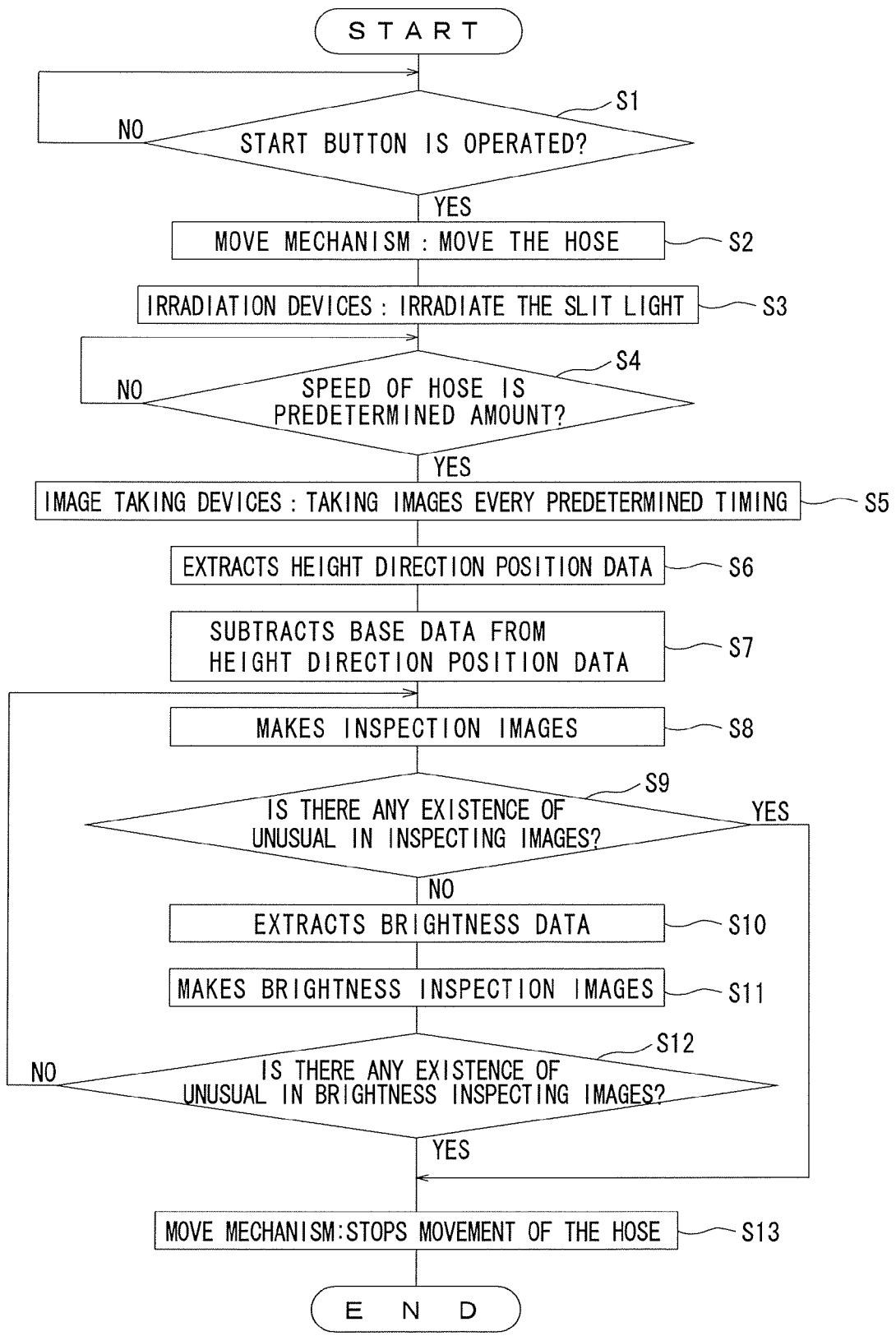
FIG. 14 is a flowchart showing operations of a controller.

FIGS. 1 to 14 show the first embodiment of the present invention. FIG. 1 is a perspective view of a principal part of an apparatus for inspecting appearance of a long-length object, FIG. 2 is a side view of a principal part of the apparatus for inspecting appearance of a long-length object, FIG. 3 is a sectional view taken on line A-A in FIG. 2, FIG. 4 is a perspective view of a principal part of a horse, FIG. 5 is an example of a taken image, FIG. 6 is a partially enlarged view of FIG. 5, FIG. 7 is an example of base data, FIG. 8 is an example of height direction position data which is given subtracting, FIG. 9 is an example of an inspection image, FIG. 10 is a perspective view of a principal part of a hose, FIG. 11 is an example of a taken image, FIG. 12 is an example of a luminance inspection image, FIG. 13 is a block diagram of the apparatus for inspecting appearance of a long-length object, and FIG. 14 is a flowchart showing operations of a controller.

This apparatus for inspecting appearance of a long-length object is equipped with two or more irradiation devices 10 which can irradiate light (hereafter, this is called slit light S) which serves as a line on an irradiated subject, a move mechanism which moves a hose H (long-length object) in its length direction, a first guide mechanism 30 and a second guide mechanism 40 for guiding the hose H, two or more image taking devices 50 capable of taking images of a lighted line L, which is formed by the slit light S of irradiation devices 10 being irradiated on the outer surface of the hose H, from a direction of forming a predetermined angle α (in this embodiment, approximately 30°) with a face of the slit light S. The hose H is formed by vulcanizing in a state in which a cloth member (not illustrated) wraps spirally an outer surface and the cloth member being removed after vulcanization. Here, since the cloth member is formed by fiber such as nylon being knitted, the remains of texture are transferred and the outer surface of the hose H becomes rough. In addition, since the cloth member is wrapped spirally so as to overlap each other, a spiral recessed portion SP (or a convex portion) is formed in a portion where the cloth member itself overlaps.

The slit light S irradiated from each irradiation device 10 is constructed of a red laser beam, and the slit light S is irradiated on the outer surface of the hose H in a line. In this embodiment, four irradiation devices 10 are provided, and mutually, respective irradiation devices 10 are arranged in intervals of approximately 90° in a circumferential direction of the hose H. In addition, each irradiation device 10 is arranged so that the face of the slit light S may cross an axial direction of the hose H approximately vertically. The slit light S irradiated from the respective irradiation device 10 is mutually connected in the circumferential direction of the hose H. That is, one lighted line L which goes around the hose H is formed in the outer surface of the hose H by the slit light S of the irradiation devices 10.

The move mechanism 20 has a pair of upper and lower belt conveyers 21. When the hose H is sandwiched and held between these belt conveyers 21 and the belt conveyers 21 rotate, the hose H moves in a length direction.

The first guide mechanism 30 has a plurality of first guide members 31 (four in this embodiment), the first guide members 31 are arranged with keeping intervals mutually in the circumferential direction of the hose H. The first guide members 31 are arranged near the lighted line L, and are arranged in an upstream of the moving direction of the hose H to the lighted line L. In addition, the respective first guide members 31 are forced on the outer surface of the hose H by air cylinders 32 (pushing mechanisms) with predetermined pushing forces respectively. A contact member 31*a* is provided in a side of each first guide member 31 near to the hose H, and the each contact member 31*a* contacts the outer surface of the hose H. The each contact member 31*a* is constructed of a low friction coefficient material whose friction coefficient with the outer surface of the hose H is 0.12 or less. An abutting surface 31*b* abutting on the hose H in the each contact member 31*a* is formed so as to extend in an axial direction of the hose H, and is formed two-fold or longer in the axial direction of the hose than a pitch P of the spiral recessed portion SP (or convex portion) in the axial direction of the hose. As an example of the low friction coefficient material, silicon, a fluororesin, super-high polymer polyethylene whose molecular weight is 1,000,000 or more, and the like are mentioned. That is, the contact surface 31*b* in contact with the hose H in the each first guide member 31 is formed in the axial direction of the hose two-fold or longer than the pitch P of the spiral recessed portion SP (or convex portion) in the axial direction of the hose, and is formed of a low friction coefficient material whose friction coefficient with the outer surface of the hose H is 0.12 or less. An auxiliary guide mechanism 33 which guides the hose H to the first guide mechanism 30 is provided in an upstream of the moving direction of the hose H to the first guide mechanism 30.

The second guide mechanism 40 has a plurality of second guide members 41 (four in this embodiment), and second guide members 41 are arranged with keeping intervals mutually in the circumferential direction of the hose H. The second guide members 41 are arranged near the lighted line L, and are arranged in a downstream of the moving direction of the hose H to the lighted line L. In addition, the respective second guide members 41 are forced on the outer surface of the hose H by air cylinders 42 (pushing mechanisms) with predetermined pushing forces respectively. A contact member 41*a* is provided in a side of each second guide member 41 near to the hose H, and the each contact member 41*a* contacts the outer surface of the hose H. The each contact member 41*a* is constructed of a low friction coefficient material whose friction coefficient with the outer surface of the hose H is 0.12 or less, and a contact surface 41*b* abutting on the hose H in the contact member 41*a* not only is formed so as to extend in the axial direction of the hose H but also is formed two-fold or longer in the axial direction of the hose than the pitch P of the spiral recessed portion SP (or convex portion) in the axial direction of the hose. As an example of the low friction coefficient material, silicon, a fluororesin, super-high polymer polyethylene whose molecular weight is 1,000,000 or more, and the like are mentioned. That is, the contact surface 41*b* in contact with the hose H in the each second guide member 41 is formed in the axial direction of the hose two-fold or longer than the pitch P of the spiral recessed portion SP (or convex portion) in the axial direction of the hose, and is formed of a low friction coefficient material whose friction coefficient with the outer surface of the hose H is 0.12 or less.

Each image taking device 50 is a two-dimensional image taking device having a plurality of pixels respectively in an X-axis direction (direction according to a width direction of the hose H), and a Y-axis direction (direction according to a height direction of the hose H) which is orthogonal to the X-axis. In this embodiment, the four image taking devices 50 are provided, and the image taking devices 50 are arranged with keeping intervals of approximately 90° mutually in the circumferential direction of the hose H. In addition, the respective image taking devices 50 are arranged by turns with the respective irradiation devices 10 in the circumferential direction of the hose H, and the respective image taking device 50 are arranged in positions which are shifted by approximately 45° in the circumferential direction of the hose H to the respective irradiation devices 10. Namely, the respective image taking devices 50 are arranged in an approximately center of the circumferential direction of the hose H to two arbitrary adjoining irradiation devices 10 in the peripheral direction of the hose H among the respective irradiation devices 10. Each image taking device 50 is equipped with a widely known photosensitivity regulating function which performs a photosensitivity adjustment individually. This photosensitivity regulating function is adjustable at two or more steps in the photosensitivity of a whole image instead of every pixel.

The respective irradiation devices 10, move mechanism 20, and respective image taking devices 50 are connected to the controller 60 which is constructed of a widely known microcomputer, and the controller 60 is connected to a widely known display unit 61, such as a liquid crystal display, and an operation section 62. The operation section 62 is equipped with a start button.

In the apparatus for inspecting appearance of a long-length object which is constructed as described above, appearance of the hose H is inspected as shown in FIG. 4 to FIG. 12 and a flowchart in FIG. 14 showing operations of the controller 60.

First, the respective guide members 31 and 41 of the guide mechanisms 30 and 40 being forced on the outer surface of the hose H with predetermined pushing forces, the hose H passes the respective guide mechanisms 30 and 40, and is held on the belt conveyers 21 of the move mechanism 20. When the start button of the operation section 62 is operated in this state (S1), the controller 60 moves the hose H by the move mechanism 20 (S2), and irradiates the slit light S toward the outer surface of the hose H by irradiation devices 10 (S3).

Then, when rotational speed of the respective belt conveyers 21 becomes predetermined rotational speed and the hose H becomes predetermined speed (35 m/min in this embodiment) (S4), the controller 60 makes the respective image taking devices 50 take images of the lighted line L on the outer surface of the hose H every predetermined time (every 1 mmsec in this embodiment), respectively (S5). That is, image taking by the respective image taking devices 50 is performed whenever the hose H moves by a predetermined distance (0.58 mm in this embodiment). Although the following describes one image taking device 50 among the respective image taking devices 50, the same processing is also performed about other image taking devices 50.

Then, the controller 60 extracts position data of the lighted line L in the height direction (Y-axis direction) corresponding to the respective width direction positions (positions of respective pixels in the X-axis direction) of the hose H from the respective taken images (for example, refer to FIG. 5) taken by the image taking device 50 (S6). For example, 68.2 is extracted as height direction position datum in a 15th pixel position from the left in the X-axis direction (X15 in FIG. 6), and 70.7 is extracted as height direction position datum in a 17th pixel position from the left in the X-axis direction (X17 in FIG. 6). In addition, height direction position data is quantified so that what is equivalent to one pixel in the Y-axis direction may become a number of 1. Furthermore, a position of a center of gravity of brightness is extracted as height direction position data by using widely known sub-pixel processing. In addition, FIG. 5 and FIG. 6 show taken images which of the lighted line L in FIG. 4 are taken, and a concave defect K is formed in the outer surface of the hose H shown in FIG. 4.

Next, the controller 60 performs subtracting of the height direction position data according to the respective width direction positions respectively with the base data (refer to FIG. 7) which are provided for every width direction position (S7), and the height direction position data (refer to FIG. 8) which is given the subtracting is obtained. For example, the height position datum after the subtracting in the 15th pixel position (X15 in FIG. 8) from the left in the X-axis direction becomes 0, and the height position datum after the subtracting in the 17th pixel position (X17 in FIG. 8) from the left in the X-axis direction becomes −1.3. Here, theoretical numerical values are used as base data, for example. The theoretical numerical values are, for example, height direction position data of respective width direction positions when the hose H has medium values of designed size and the spiral recessed portions SP (or convex portions) are not formed. That is, the base data is numerical data provided every width direction position so as to correspond to the outer peripheral surface shape of the hose H.

Next, the controller 60 arranges the respective height direction position data, which is given the subtracting, in image-taking order, makes an inspection image (refer to FIG. 9) on the basis of a predetermined image color standard, and makes the display unit 61 display the inspection image (S8). Here, the height direction position data after the subtracting which is equivalent to the predetermined number of times (for example, 128 times) of image taking is used for one sheet of inspection image. In addition, as the predetermined image color standard, a standard that the smaller a numerical value of position data is, the deeper a color is used. In this case, a color of a concave portion becomes deep in comparison with other portions in the outer surface of the hose H, and a color of a convex portion becomes light in comparison with other portions in the outer surface of the hose H. That is, as shown in FIG. 9, colors of portions of the spiral recessed portions SP and defect K become deep in comparison with other portions.

Then, on the basis of the predetermined judging standard, the controller 60 judges the presence of unusual on the made inspection image (S9). Here, tolerable ranges of the pitch P of the spiral recessed portion SP and an angle γ to the length direction of the hose H are determined as the predetermined judging standard. By this, when the recessed portion which appears on the inspection image is in the tolerable ranges of the pitch P and angle γ, a judged result becomes normal, and when the recessed portion which appears on the inspection image exceeds the tolerable ranges of the pitch P and angle γ, a judged result becomes unusual. Furthermore, in the predetermined judging standard, when there is a portion projecting across the tolerable range rather than other portions, the judged result becomes unusual. For this reason, as shown in FIG. 9, when a recessed portion by the defect K appears besides the spiral recessed portion SP and the pitch P between the recessed portion by the defect K and the spiral recessed portion SP is not in the tolerable range or the angle γ of the recessed portion by the defect K is not in the tolerable range, the judged result becomes unusual as mentioned above.

On the other hand, the controller 60 extracts brightness data of the lighted line L corresponding to the respective width direction positions (positions of respective pixels in the X-axis direction) of the hose H from the respective taken images (for example, refer to FIG. 11) taken by the image taking device 50 (S10). In addition, FIG. 11 shows the taken image which of the lighted line L in FIG. 10 is taken. A foreign material D with a color lighter than that of the outer surface of the hose H sticks to the outer surface of the hose H shown in FIG. 10.

Next, by arranging the brightness data of the respective taken images in the image-taking order on the basis of the predetermined image color standard, the controller 60 makes a brightness inspection image (refer to FIG. 12), and makes the display unit 61 display the brightness inspection image (S11). Here, the brightness data which is equivalent to the predetermined number of times (for example, 128 times) of image taking is used for one sheet of brightness inspection image. In addition, when a standard that the smaller a numerical value of luminance data is, the deeper a color is used as the predetermined image color standard, a normal portion (black portion) of the outer surface of the hose H becomes a deep color, and a portion with a color different from the outer surface of the hose becomes light. In the case of FIG. 12, a color of the portion to which the foreign material D sticks is thin in comparison with those of other portions.

Then, on the basis of the predetermined judging standard, the controller 60 judges the presence of unusual in the made brightness inspection image (S12). Here, in the above-mentioned predetermined judging standard, if an area of a lighter-colored portion than other portions on the brightness inspection image is below a predetermined amount, a judged result becomes normal, and if the area of the lighter-colored portion than other portions exceeds the predetermined amount, a judged result becomes unusual. For this reason, as shown in FIG. 12, if the color of the portion of the foreign material D is lighter than those of other portions and the area of that portion exceeds the predetermined amount, a judged result becomes unusual.

Next, when the judged result becomes unusual at step S9 or step S12, the controller 60 stops movement of the hose H by the move mechanism 20 (S13).

In this embodiment, since slit light S is irradiated toward the outer surface of the hose H, the lighted line L which is formed by the slit light S being radiated on the outer surface of the hose H shows contour of the hose H in the position correctly. In addition, since an image of the lighted line is taken from the direction of forming the predetermined angle α with the face of the slit light S, an image of the contour of the hose H in the position of the lighted line is taken correctly. Furthermore, in this embodiment, since an image of the lighted line L is taken every specified time with the hose H being moved in the length direction to the respective irradiation devices 10, images of the contour of the hose H are taken continuously and correctly over the length direction of the hose H. In addition, the height direction position data of the lighted line L according to the respective width direction positions of the hose H is extracted from the respective taken images respectively, and the subtracting of the position data is performed respectively with the base data provided every width direction position according to the outer peripheral surface shape of the hose H. For this reason, an arc shape of the outer surface of the hose H is canceled from the height direction position data. Thereby, the height direction position data after subtracting shows clearly the unevenness, defect, and the like in the outer surface of the hose H. Furthermore, the height direction position data of respective taken images which are given the subtracting is put in image-taking order, an inspection image is made on the basis of the predetermined image color standard, and the presence of the unusual on the inspection image is judged on the basis of the predetermined judging standard. For this reason, in comparison with a case in which an inspection image is made without canceling the arc shape of the outer surface of the hose H, the unevenness, defect, and the like in the outer surface of the hose H become clear on the inspection image. Hence, it is possible to conduct correctly the appearance inspection of the hose H which is formed by vulcanizing in a state in which a cloth member wraps spirally the outer surface.

In addition, by each of brightness data of the lighted line L, which corresponds to each width direction position of the hose H, being extracted every taken image and the brightness data of the each taken image being arranged in image-taking order on the basis of the predetermined image color standard, a brightness inspection image is made. Furthermore, the existence of unusual on the brightness inspection image on the basis of the predetermined judging standard is judged. For this reason, it is possible to detect not only the unevenness and defect in the outer surface, but also a foreign material, which sticks to the outer surface of the hose H, exposure of a reinforcement, and the like.

In this embodiment, two or more guide members 31 and 41 are provided in a circumferential direction of the hose H near the imaging position (lighted line L) by the image taking device 50 with intervals being kept, and the respective guide members 31 and 41 touch the outer surface of the hose H respectively. For this reason, the hose H is guided by the respective guide members and 41 near an image taking device 50 so as not to move vertically and horizontally. In addition, contact surfaces 31b and 41b of the respective guide members 31 and 41 are formed two-fold or longer in the axial direction of the hose than the pitch P of the spiral recessed portion SP (or convex portion) in the axial direction of the hose. Hence, when the spiral recessed portion SP (or convex portion) passes the respective guide members 31 and 41, the hose H does not move vertically and horizontally. Furthermore, the contact surfaces 31b and 41b of the respective guide members 31 and 41 are formed of a low friction coefficient material whose friction coefficient with the outer surface of the hose H is 0.12 or less. Thereby, the hose H moves smoothly on the respective guide members 31 and 41.

That is, the hose H is guided by the respective guide members 31 and 41 near the image taking position by the image taking device 50 so as not to move vertically and horizontally. For this reason, when the spiral recessed portion SP (or convex portion) passes the respective guide members 31 and 41, the hose H does not move vertically and horizontally, but moves smoothly on the respective guide members 31 and 41. Hence, when images of the outer surface of the hose H which has the spiral recessed portion SP (or convex portion) in the outer surface and moves in the axial direction are taken, it is possible to stabilize the vertical and horizontal position of the hose H in the image taking position. Hence, for example, when the hose H in the image taking position moves vertically, a vertical position of the lighted line L on a taken image changes by the movement, and generation of an exact inspection image is hindered. On the other hand, this embodiment can stabilize the vertical and horizontal position of the hose H in an image taking position. For this reason, it is possible to make an always exact inspection image, and it is very advantageous when improving accuracy of an appearance inspection.

In addition, in comparison with a case in which respective guide members 31 and 41 are formed from two or more rollers, it is possible to lessen a thickness dimension (dimension of the hose H in a radial direction) of the respective guide members 31 and 41. Hence, it is possible to suppress entrance of the respective guide members 31 and 41 into an image taking range of the respective image taking devices 50. That is, it is possible to shorten a distance between the respective guide members 31 and 41 and the lighted line L, and it is possible to make correctly the inspection image of an easy-to-be-bent material which has flexibility like the hose H.

Furthermore, the respective guide members 31 and 41 are forced on the outer surface of the hose H by air cylinders 32 and with predetermined pushing forces respectively. For this reason, even if a vertical direction or horizontal external force is applied to the hose H, the hose H does not move vertically or horizontally easily. That is, this is extremely advantageous to stabilize the vertical and horizontal position of the hose H in an image taking position.

Moreover, in this embodiment, the first guide member 31 and second guide member 41 are provided respectively in an upstream and a downstream of the moving direction of the hose H to the image taking position (lighted line L) by the image taking device 50. On the other hand, it is also possible to construct this embodiment so that only the upstream of the moving direction of the hose H may be guided by the respective first guide members 31, or it is also possible to construct this embodiment so that only the downstream of the moving direction of the hose H may be guided by the respective second guide members 41. Also in these cases, similarly to the above-mentioned, it is possible to stabilize the vertical and horizontal position of the hose H at the image taking position.

Figure 15:
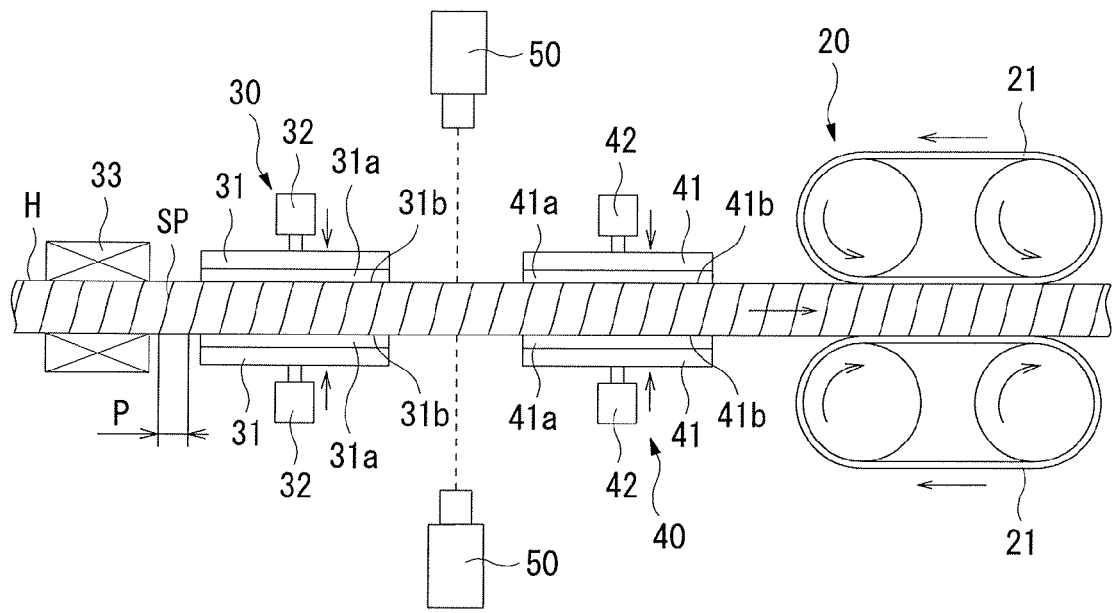
FIG. 15 is a side view of a principal part of an apparatus for inspecting appearance of a long-length object which shows a first modified example of the first embodiment.

In addition, in this embodiment, the lighted line L is formed on the outer surface of the hose H, images of the lighted line L are taken by the respective image taking devices 50, an inspection image is made from the taken images, and the presence of the unusual on the inspection image is judged. On the other hand, it is also possible to construct this embodiment so that images of the outer surface of the hose H may be taken by the respective image taking device 50 and the taken images may be used as an inspection image (refer to FIG. 15).

Figure 16:
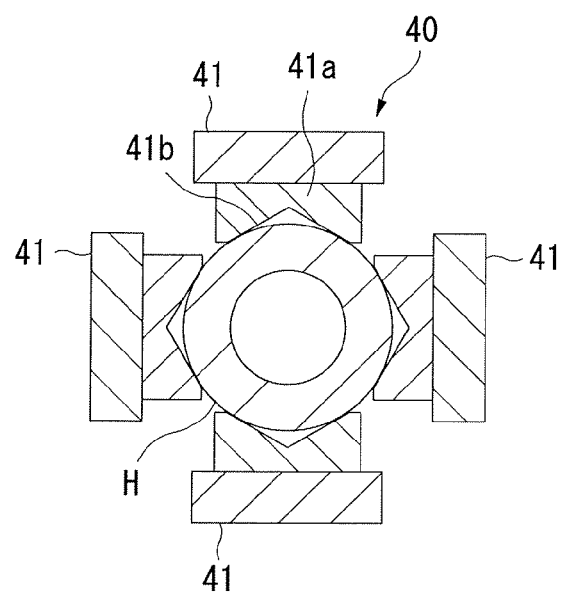
FIG. 16 is a sectional view of a second guide mechanism which shows a second modified example of the first embodiment.

Furthermore, in this embodiment, the abutting surfaces 31b and 41b of the respective guide members 31 and 41 are formed planarly as shown in FIG. 3. On the other hand, as shown in FIG. 16, it is also possible to form in the abutting surfaces 31b and 41b each recessed portion which extends in the axial direction of the hose H, and to regulate movement of the hose H in a width direction by the each recessed portion.

In this embodiment, one ray of lighted line L is formed on the outer surface of the hose H with the slit light S of two or more irradiation devices 10. In addition, the respective image taking devices 50 are arranged in an approximately center of the peripheral direction of the hose H to two arbitrary adjoining irradiation devices 10 in the peripheral direction of the hose H among the respective irradiation devices 10. Hence, it is possible to make luminance of the lighted line L, which is visible from the respective image taking devices 50, approximately uniform over the width direction of the hose H.

Namely, when images of the lighted line L with which is formed by the slit light S being irradiated on the outer surface of the hose H which has an approximately circular section are taken by the respective image taking devices 50, it is possible to make luminance of the lighted line L, which is visible from the respective image taking devices 50, approximately uniform over the width direction of the hose H. Hence, it is possible to perform photosensitivity adjustments of the respective image taking devices 50 easily and appropriately.

That is, when luminance of the lighted line L which is visible from the respective image taking devices 50 differs remarkably over the width direction of the hose H and the photosensitivity adjustments of the respective image taking devices 50 cannot be performed appropriately, it is not possible to extract correctly the height direction position of the lighted line L in taken images (refer to FIG. 5). Namely, the appearance inspection of the hose H is hindered. In addition, when the luminance of the lighted line L which is visible from the respective image taking devices 50 differs remarkably over the width direction of the hose H, unless the photosensitivity adjustments of the respective image taking devices 50 are performed every pixel, it is not possible to extract correctly luminance changes of the lighted line L because of color difference of the outer surface of the hose H in the taken images (refer to FIG. 11). That is, the appearance inspection of the hose H is hindered. On the other hand, in this embodiment, it is possible to make luminance of the lighted line L, which is visible from the respective image taking devices 50, approximately uniform over the width direction of the hose H, and it is possible to perform photosensitivity adjustments of the respective image taking devices 50 easily and appropriately. Hence, it is very advantageous when conducting an appearance inspection of the hose H correctly.

In addition, the same number of respective image taking devices 50 are arranged as the number of respective irradiation devices 10 and the respective image taking device 50 are arranged by turns with the respective irradiation devices 10 in the peripheral direction of the hose H. Hence, it is possible to inspect the outer surface of the hose H at once over all the circumference.

Furthermore, four irradiation devices 10 are provided in this embodiment. On the other hand, it is also possible to provide two or three irradiation devices 10, and it is also possible to provide five or more irradiation devices 10.

Figure 17:
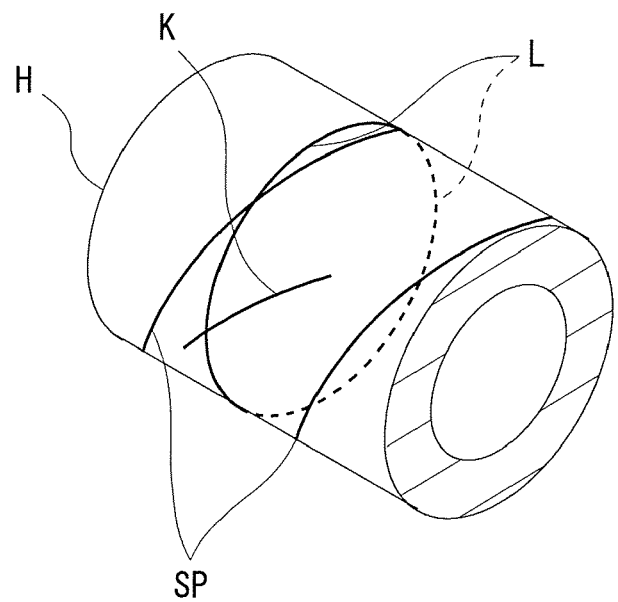
FIG. 17 is a perspective view of a principal part of a hose showing a second embodiment of the present invention.
Figure 18:
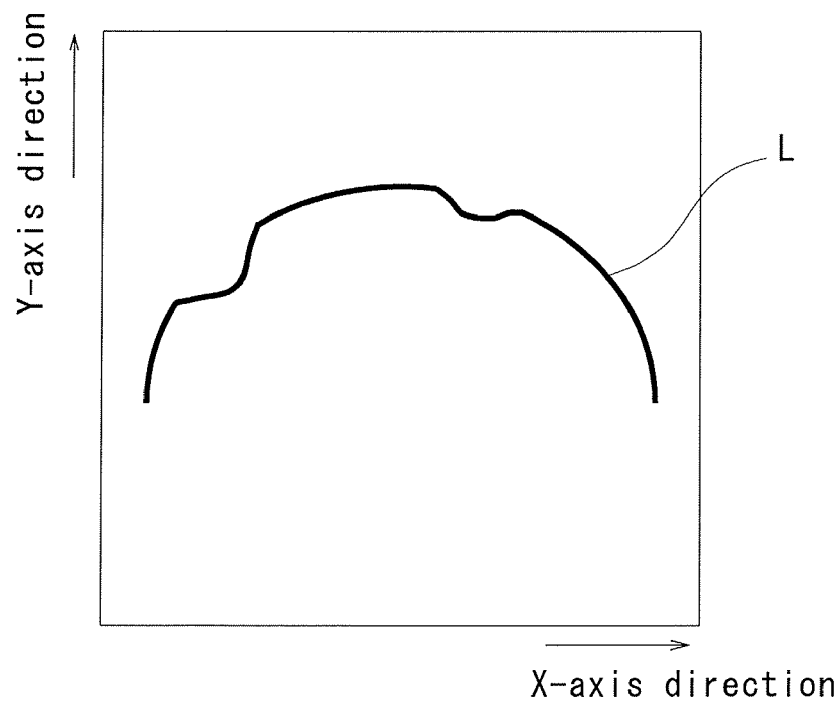
FIG. 18 is an example of a taken image.
Figures 19, 20:
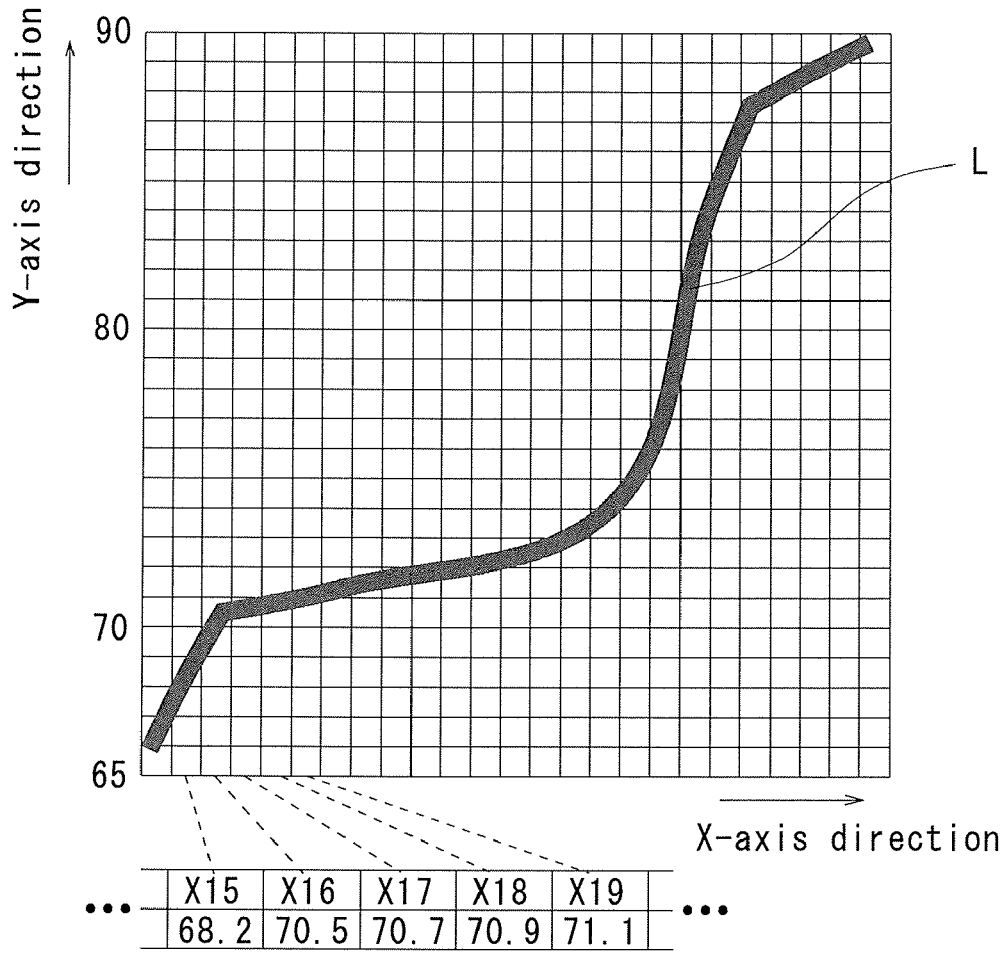
FIG. 19 is a partial enlarged view of FIG. 18, and an example of height direction position data.
FIG. 20 is an example of base data.
Figure 21:
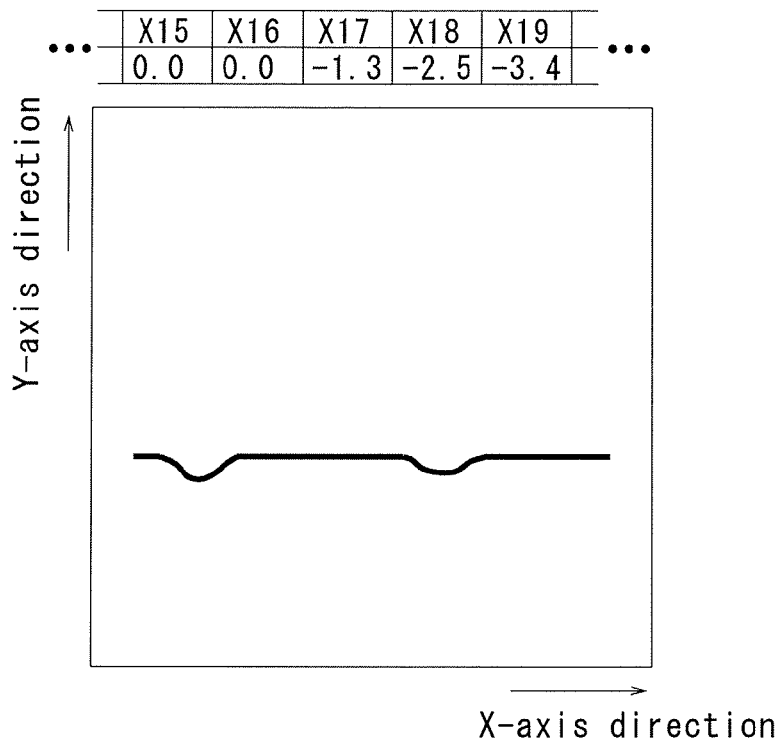
FIG. 21 is an example of height direction position data which is given subtracting.
Figure 22:
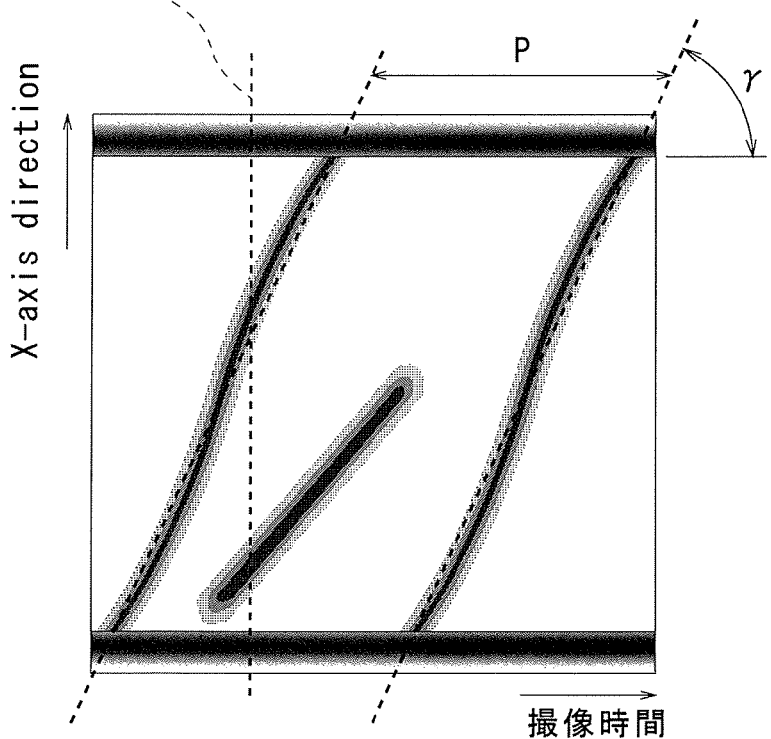
FIG. 22 is an example of an inspection image.
Figure 23:
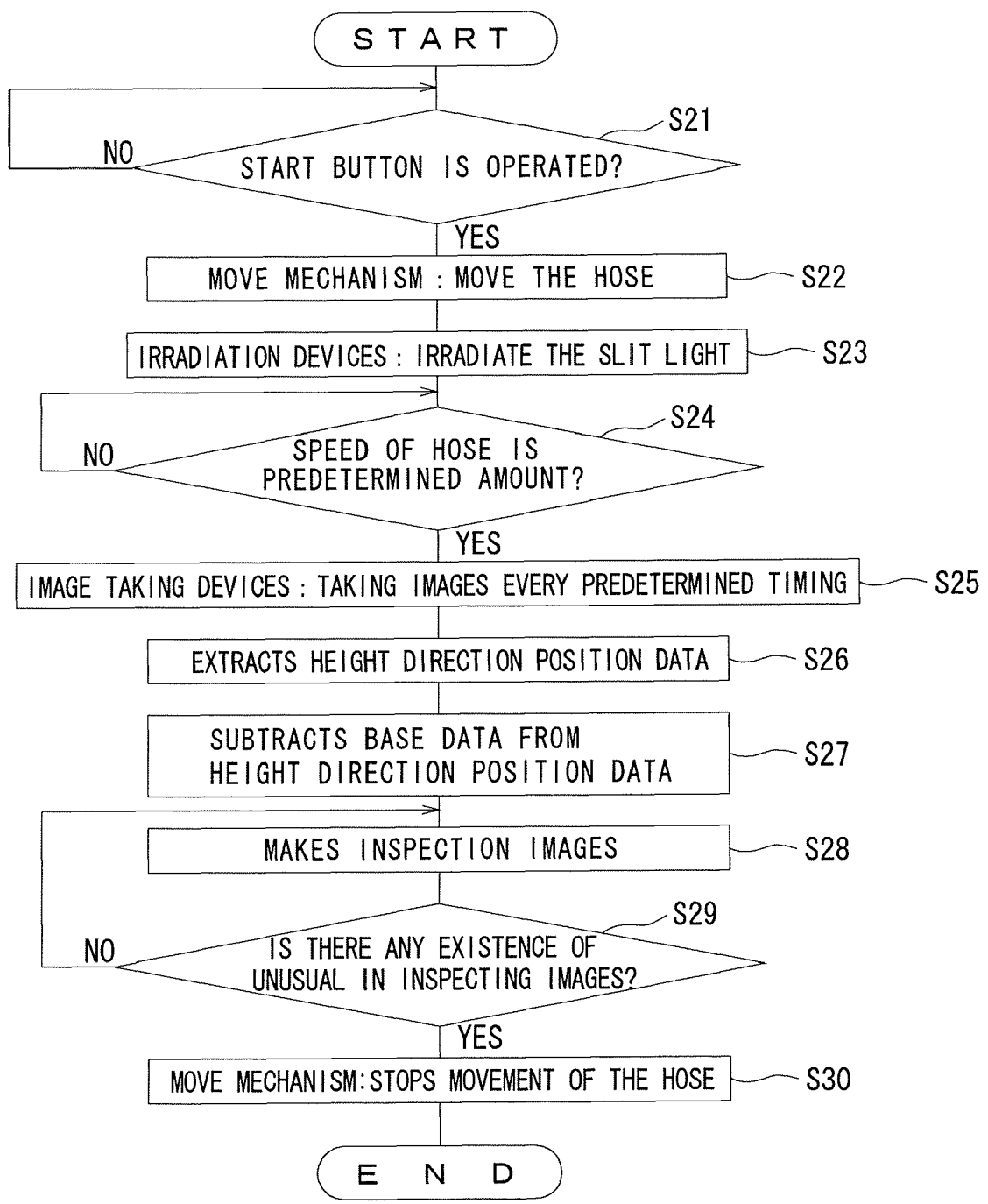
FIG. 23 is a flowchart showing operations of the controller.

FIGS. 17 to 23 show a second embodiment of the present invention. FIG. 17 is a principal part perspective view of a hose, FIG. 18 is an example of a taken image, FIG. 19 is a partially enlarged view of FIG. 5, and an example of height direction position data, FIG. 20 is an example of base data, FIG. 21 is an example of the height direction position data which is given subtracting, FIG. 22 is an example of an inspection image, and FIG. 23 is a flowchart showing operations of a controller. In addition, the same reference symbols are assigned to component parts equivalent to those of the first embodiment.

The apparatus for inspecting appearance of a long-length object which is shown in the second embodiment has the two or more irradiation devices 10, move mechanism 20, respective guide mechanisms 30 and 40, two or more image taking devices 50, controller 60, display unit 61, and operation section 62, which are equivalent to those of the first embodiment.

In the apparatus for inspecting appearance of a long-length object which is constructed as described above, appearance of the hose H is inspected as shown in FIG. 17 to FIG. 22 and a flowchart in FIG. 23 showing operations of the controller 60.

First, in a state in which the hose H passes the respective guide mechanisms 30 and 40 and is held on the respective belt conveyers 21 of the move mechanism 20, when the start button of the operation section 62 is operated (S21), the controller 60 moves the hose H by the move device 20 (S22), and irradiates the slit light S toward the outer surface of the hose H by respective irradiation devices 10 (S23).

Then, when rotational speed of the respective belt conveyers becomes a predetermined rotational speed and the hose H becomes predetermined speed (35 m/min in this embodiment) (S24), the controller 60 makes the respective image taking devices 50 take images of the lighted line L on the outer surface of the hose H every predetermined timing (every 1 mmsec in this embodiment), respectively (S25). That is, image taking by the respective image taking devices 50 is performed whenever the hose H moves by a predetermined distance (0.58 mm in this embodiment). Although the following describes one image taking device 50 among the respective image taking devices 50, the same processing is also performed about other image taking devices 50.

Next, the controller 60 extracts position data of the lighted line L in the height direction (Y-axis direction) according to the respective width direction positions (positions of respective pixels in the X-axis direction) of the hose H from the respective taken images (for example, refer to FIG. 18) taken by the image taking device 50 (S26). For example, 68.2 is extracted as height direction position data in a 15th pixel position from the left in the X-axis direction (X15 in FIG. 19), and 70.7 is extracted as height direction position data in a 17th pixel position from the left in the X-axis direction (X17 in FIG. 19). In addition, height direction position data is quantified so that what is equivalent to one pixel in the Y-axis direction may become a number of 1. Furthermore, a position of a center of gravity of luminance is extracted as height direction position data by using widely known sub-pixel processing. In addition, FIG. 18 and FIG. 19 show taken images which of the lighted line L in FIG. 17 are taken, and a concave defect K is formed in the outer surface of the hose H shown in FIG. 17.

Then, the controller 60 performs subtracting of the height direction position data according to the respective taken image data respectively with the base data which are provided for every width direction position (S27). This base data is made by averaging height direction position data of the subtraction object, and a predetermined number of height direction position data whose image-taking orders are near to that of the height direction position data every width direction position of the hose H. Specifically, for example, a predetermined number (t1 to t128 in this embodiment) of height direction position data before subtracting whose image-taking orders are continuous is dealt as one group. A first half (t1-t64) of height direction position data in the group is averaged every width direction position (position of each pixel in an X-axis direction) of the hose H, and a first half of base data, Av1 are made. In addition, a second half (t65 to t128) of height direction position data is averaged every width direction position of the hose H, and a second half of base data, Av2 are made (refer to FIG. 20). In addition, the subtracting of the first half (t1 to t64) of height direction position data is performed with the first half of base data, Av1, and the subtracting of the second half (t65 to t128) of height direction position data is performed with the second half of base data, Av2.

Next, the controller 60 arranges the respective height direction position data, which is given the subtracting, in image-taking order, makes an inspection image (refer to FIG. 22) on the basis of a predetermined image color standard, and makes the display unit 61 display the inspection image (S28). Here, the height direction position data after the subtracting which is equivalent to the above-described one group (t1 to t128) is used for one sheet of inspection image. In addition, as the predetermined image color standard, a standard that the smaller a numerical value of position data is, the deeper a color is used. In this case, a color of a concave portion becomes deep in comparison with other portions in the outer surface of the hose H, and a color of a convex portion becomes light in comparison with other portions in the outer surface of the hose H. That is, as shown in FIG. 22, colors of portions of the spiral recessed portions SP and defect K become deep in comparison with other portions.

Then, on the basis of the predetermined judging standard, the controller 60 judges the presence of unusual in the made inspection image (S29). Here, tolerable ranges of the pitch P of the spiral recessed portion SP and an angle γ to the length direction of the hose H are determined as the predetermined judging standard. For this reason, when the recessed portion which appears on the inspection image is in the tolerable ranges of the pitch P and angle γ, a judged result becomes normal, and when the recessed portion which appears on the inspection image exceeds the tolerable ranges of the pitch P and angle γ, a judged result becomes unusual. Furthermore, in the predetermined judging standard, if there is a portion projected across the tolerable range rather than other portions, a judged result become unusual. Hence, as shown in FIG. 22, when a recessed portion by the defect K appears besides the spiral recessed portions SP and the pitch P between the recessed portion by the defect K and the spiral recessed portion SP is not in the tolerable range or the angle γ of the recessed portion by the defect K is not in the tolerable range, the judged result becomes unusual as mentioned above.

Next, when the judged result becomes unusual at step S29, the controller 60 stops movement of the hose H by the move mechanism 20 (S30).

In this embodiment, since slit light S is irradiated toward the outer surface of the hose H, the lighted line L which is formed by the slit light S being radiated on the outer surface of the hose H shows contour of the hose H in the position correctly. In addition, since an image of the lighted line L is taken from the direction of forming the predetermined angle α with the face of the slit light S, an image of the contour of the hose H in the position of the lighted line L is taken correctly. Furthermore, in this embodiment, since an image of the lighted line L is taken every specified time with the hose H being moved in the length direction to the respective irradiation devices 10, images of the contour of the hose H are taken continuously and correctly over the length direction of the hose H. In addition, the height direction position data of the lighted line L according to the respective width direction positions of the hose H is extracted from the respective taken images respectively, and the subtracting of the respective height direction position data is performed respectively with the base data provided every width direction position of the hose H. Furthermore, the respective height direction position data which is given the subtracting is put in image-taking order, an inspection image is made on the basis of the predetermined image color standard, and the presence of the unusual on the inspection image is judged. At this time, the base data is made by averaging height direction position data of the subtraction object, and a prescribed number of height direction position data whose image-taking orders are near to that of the height direction position data every width direction position of the hose H. For this reason, an arc shape of the outer surface of the hose H is canceled from the height direction position data. Namely, even when the hose H has waviness in the length direction, a part for the waviness is canceled from height direction position data, and the height direction position data after subtracting shows clearly only the unevenness and defect of the outer surface of the hose H. That is, when the appearance inspection of the hose H is conducted like this embodiment, even if the respective guide mechanisms 30 and 40 guide the hose H, the hose H winds a little in the length direction. On the other hand, in this embodiment, when making an inspection image, it is possible to set an image color standard regardless of an outer peripheral surface shape or presence of the waviness of the hose H. Hence, it is very advantageous when conducting the appearance inspection in high accuracy.

In addition, in this embodiment, a predetermined number (t1 to t128) of height direction position data before subtracting whose image-taking orders are continuous is dealt as one group. In addition, when one sheet of inspection image is made using the height direction position data after the subtracting for one group (t1 to t128), the base data is made by averaging height direction position data of objects of subtracting and a predetermined image-taking number of ones among height direction position data before the subtracting which is used in the same inspection picture as the height direction position data, every width direction position. Hence, an arc shape of the outer surface of the hose H can be canceled from the height direction position data. Namely, even when the hose H has waviness in the length direction, waviness-equivalence can be canceled from the height direction position data.

Furthermore, one sheet of inspection image is made in this embodiment from the height direction position data after the subtracting for one group (t1 to t128). On the other hand, it is also possible to make an inspection image continuously without delimiters. Also in this case, the base data can be made by averaging the height position data of the subtraction object, and prescribed number of height position data before subtracting, whose image-taking orders are near to that of the height position data, every width position of the hose H.

Figures 24, 25:
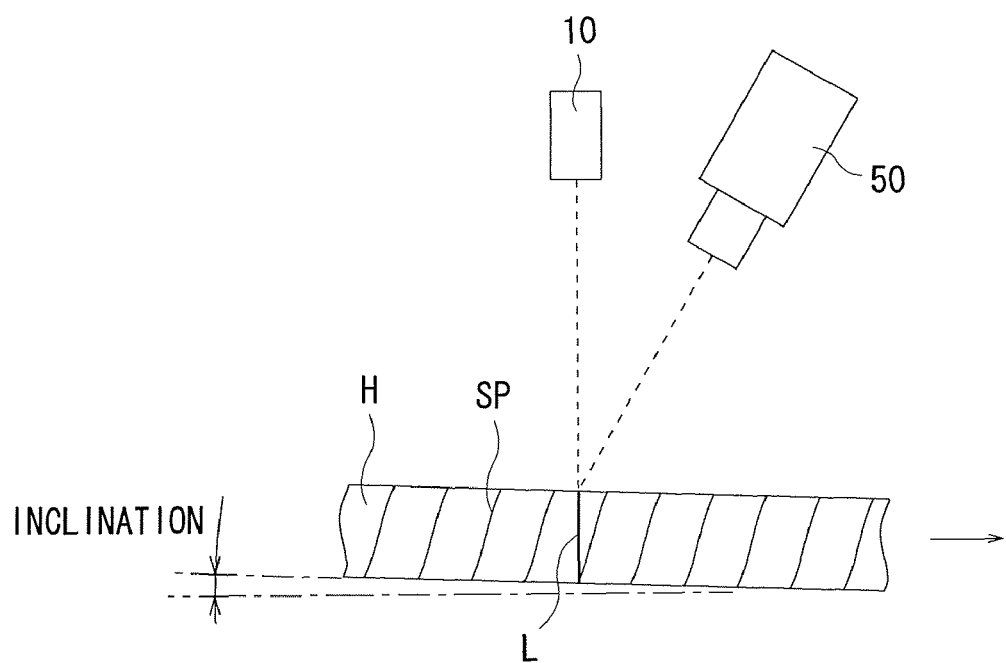
FIG. 24 is an example of base data showing the third embodiment of the present invention.
FIG. 25 is a side view of a principal part of the apparatus for inspecting appearance of a long-length object.

FIGS. 24 to 26 show a third embodiment of the present invention. FIG. 24 is an example of base data, FIG. 25 is a side view of a principal part of an apparatus for inspecting appearance of a long-length object, and FIG. 26 is an example of measurement of a height direction position in X15. In addition, the same reference symbols are assigned to component parts equivalent to those of the second embodiment.

The appearance inspection apparatus according to the third embodiment is equipped with the two or more irradiation devices 10, move mechanism 20, respective guide mechanisms 30 and 40, two or more image taking devices 50, controller 60, display unit 61, and operation section 62, which are equivalent to those of the second embodiment. In addition, this appearance inspection apparatus conducts an appearance inspection of the hose H like the flowchart in FIG. 23 of the second embodiment.

In the second embodiment, the base data is made by averaging height direction position data of the subtraction object, and prescribed number of height direction position data whose image-taking orders are near to that of the height direction position data every width direction position of the hose H. On the other hand, in the third embodiment, the base data is made to the respective height direction position data respectively. That is, each base data is made by averaging a predetermined number of height direction position data before subtracting, where height direction position data of the subtraction object is an approximate center of image-taking order, every width direction position of the hose H. In addition, the subtracting of the respective height direction position data is performed with respective base data.

Specifically, similarly to the second embodiment, a predetermined number (t1 to t128 in this embodiment) of height position data before subtracting whose image-taking orders are continuous is dealt as one group, and, for example, by averaging the prescribed number (t2 to t10) of height direction position data, in which height direction position data in t6 is a center of image-taking order, every width direction position (position of each pixel in the X-axis direction) of the hose H, sixth base data Av6 is made (refer to FIG. 24). In addition, the subtracting of the height direction position data in t6 is performed with the sixth base data Av6. In addition, base data corresponding to other height direction position data is made similarly.

Figure 26A:
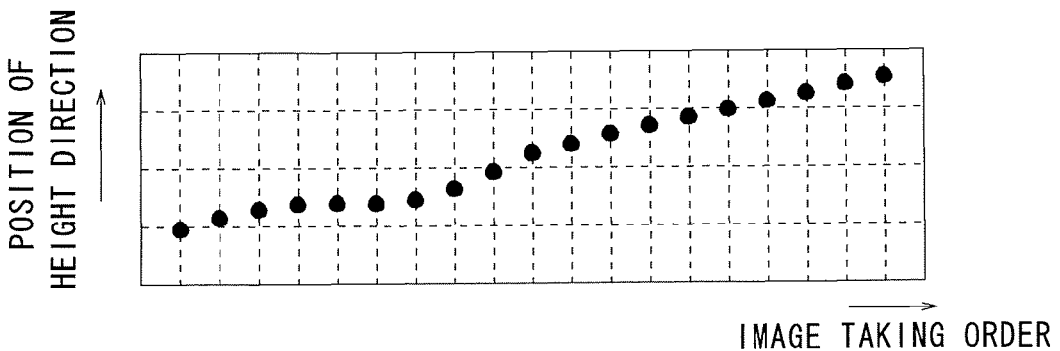
FIG. 26 is an example of a measurement result of height direction position in X15.
Figure 26B:
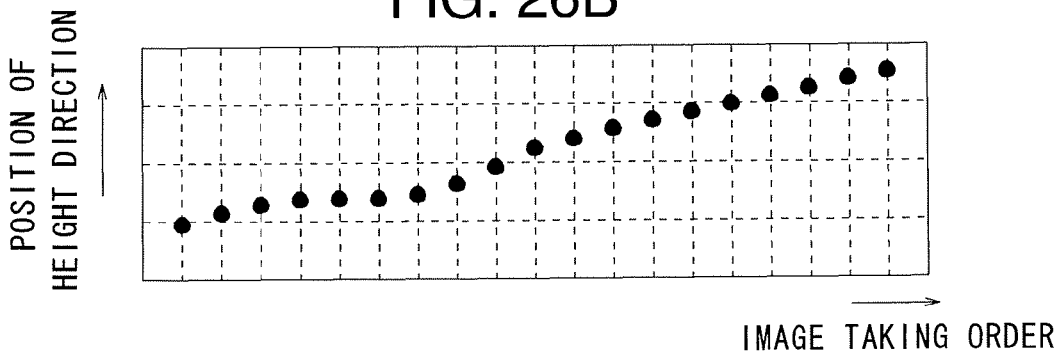
Figure 26C:
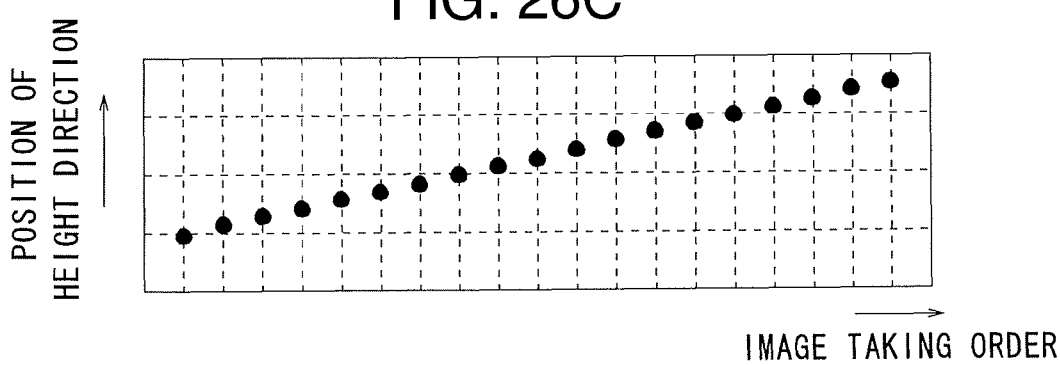
Figure 26D:
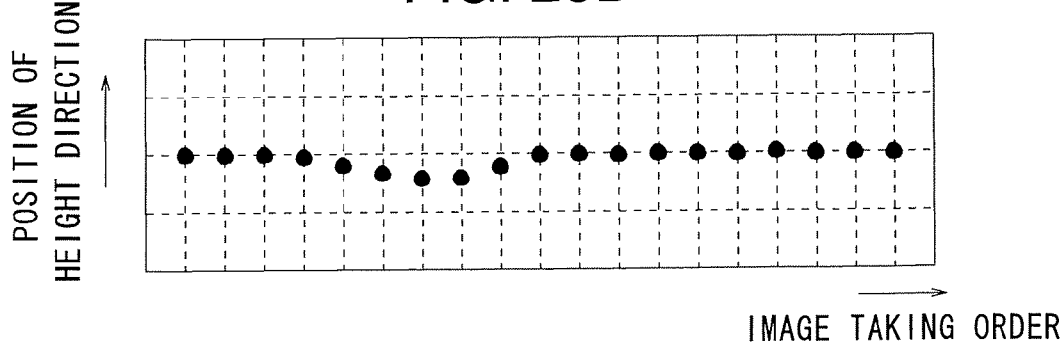

Here, when the hose H is accompanied by waviness, the hose H inclines in a length direction partially. Namely, when an image of the hose H which is oblique as shown in FIG. 25 is taken by the image taking device 50, for example, when height direction position of the lighted line L in a 15th pixel position (XI5) from the left in an X-axis direction is put in order in image-taking order, as shown in FIG. 26A, the height direction position changes gradually according to an inclination of the hose H. When the subtracting of respective height direction position data in FIG. 26A is performed with an arithmetic mean of the respective height direction position data in FIG. 26A, as shown in FIG. 26B, slant components of the hose H remains in the respective height direction position data after the subtracting. On the other hand, as shown in FIG. 24, when base data is made every height direction position data, values of the respective base data in X15 changes gradually according to the inclination of the hose H as shown in FIG. 26C. In addition, when the subtracting is performed by base data in FIG. 26C, as shown in FIG. 26D, slant components of the hose H are cancelled from the respective height direction position data after the subtracting.

That is, base data is made every height direction position data, That is, each base data is made by averaging a prescribed number of height direction position data before subtracting, where height direction position data of the subtraction object is an approximate center of image-taking order, every width direction position of the hose H. In addition, the subtracting of the respective height direction position data is performed with respective base data. For this reason, similarly to the first and second embodiments, an arc shape of the outer surface of the hose H can be canceled. In addition, even when the hose H has waviness in the length direction, a part for the waviness is canceled from height direction position data, and the height direction position data after the subtracting shows clearly only the defect of the outer surface of the hose H. Furthermore, when the hose H has waviness in the length direction, when conducting the appearance inspection of a portion inclined by the waviness, waviness components can be canceled more correctly from the height direction position data. Hence, it is very advantageous when conducting the appearance inspection in high accuracy.

In addition, one sheet of inspection image is made in this embodiment using the height direction position data after the subtracting for one group (t1 to t128). On the other hand, it is also possible to make an inspection image continuously without delimiters. Also in this case, each base data is made by averaging a prescribed number of height direction position data before subtracting, where height direction position data of the subtraction object is an approximate center, every width direction position of the hose H. That is, it is possible to perform the subtracting of the respective height direction position data with the respective base data.

Furthermore, in the first, second, and third embodiments, the hose H and the respective irradiation devices 10 move relatively by moving the hose H by the move mechanism 20. On the other hand, it is also possible to move the hose H and the respective irradiation devices 10 relatively by moving the respective irradiation devices 10 in the length direction of the hose H instead of moving the hose H.

In addition, in the first, second, and third embodiments, one sheet of inspection image or one sheet of luminance inspection image is made with a predetermined image taking number (for example, 128 times) of position data or luminance data which is given the subtracting. In addition, the inspection image or luminance inspection image is continuously made according to movement of the hose H. In this case, it is also possible to overlap, for example, position data of the inspection image, made later, with position data of the inspection image made previously. Thereby, overlooking of the unevenness and defect which appear with ranging over two sheets of inspection images is prevented, and hence, it is very advantageous when conducting an appearance inspection of the hose H correctly.

Furthermore, in the first, second, and third embodiments, respective height direction position data is put in order in image-taking order, and an inspection image classified by color on the basis of the predetermined image color standard is made. On the other hand, it is also possible to arrange respective height direction position data in image-taking order, and to make a three-dimensional inspection image on the basis of a predetermined standard.

Moreover, in the first, second, and third embodiments, the defect K of the outer surface of the hose H appears on an inspection image. On the other hand, when unevenness arises in the outer surface of the hose H by unusual in wrapping of a cloth member, the unevenness also appears on an inspection image. Even in this case, when the unevenness does not exist in the tolerable range of the pitch P and angle γ which are mentioned above, the inspection image is judged to be unusual.

In addition, in the first, second, and third embodiments, an appearance inspection of the hose H which has spiral recessed portions SP (or convex portions) in an outer surface is conducted. On the other hand, it is also possible to inspect appearance of an electric wire and other long-length objects, which have a spiral recessed portion or convex portion in an outer surface, by the first to third embodiments.

The preferred embodiments described in this specification are illustrative and not restrictive. The scope of invention is given by the appended claims, and all changes and modifications included in the meaning of claims are embraced in the present invention.

The invention claimed is:

1. A method for inspecting appearance of a long-length object formed by vulcanizing in a state in which a cloth member wraps spirally an outer surface of the long-length object and removing said cloth member from said outer surface after vulcanization, the method comprising the steps of:
   irradiating a slit light onto outer surface of the long-length object by a light source, moving the long-length object relative to the light source and the long-length object relatively in the length direction of the long-length object, and taking images of a lighted line, formed on the outer surface of the long-length object by irradiated slit light, from a direction forming an angle relative to a face of the slit light every predetermined timing;
   extracting each of height direction position data of the lighted line, which correspond respectively to a plurality of width direction positions of the long-length object, with respect to every taken image;
   subtracting base data, which are provided to each of the width direction positions according to a shape of the outer surface of the long-length object, from each of the height direction position data, which correspond to each of the width direction positions;
   making an inspection image by arranging subtracted height direction position data of each taken image in image-taking order so as to conform to a predetermined color standard; and
   judging existence of unusual on the inspection image on the basis of a predetermined judging standard,
   wherein, a guide mechanism guides the long-length object at a position which is upstream side of the moving direction of the long-length object relative to said lighted line, the guide mechanism has a plurality of guide members which are arranged with intervals in the circumferential direction of the long-length object and each of the guide members is provided so as to be pushed on the outer surface of the long-length object.

2. The method for inspecting appearance of a long-length object according to claim 1, further comprising:
   extracting a plurality of brightness data of the lighted line from each taken image respectively so that each brightness datum corresponds respectively to the plurality of width direction positions of the long-length object;
   making a brightness inspection image by arranging said brightness data of said taken images conformity to the order of taking images so as to conform to a predetermined color standard; and
   judging existence of unusual on the brightness inspection image based on a predetermined judging standard.

3. The method for inspecting appearance of a long-length object according to claim 1, wherein
   the base data are made by averaging the height direction position data of a certain taken image, which are objects of subtracting, and a predetermined image-taking number of height direction position data, which are taken near the image-taking of said height direction position data and are not done by subtracting, for every width direction position.

4. The method for inspecting appearance of a long-length object according to claim 1, wherein
   the base data are made by averaging the height direction position data of a certain taken image, which are objects of subtracting, and a predetermined image-taking number of height direction position data, which are used in a same inspection image with said height direction position data and are not done by subtracting, for every width direction position.

5. The method for inspecting appearance of a long-length object according to claim 1, wherein
   said base data are provided corresponding respectively to each of said taken images, and
   the base data are made by averaging a predetermined image-taking number of height direction position data including the height direction position data of a certain taken image, which are objects of subtracting and taken at the center of the image-taking order of said predetermined image-taking number of height direction position data, for every width direction position.

6. An apparatus for inspecting appearance of a long-length object formed by vulcanizing in the state in which a cloth member wraps spirally an outer surface of the long-length object and removing said cloth member from said outer surface, the apparatus comprising:
   a light source for irradiating a slit light onto the outer surface of the long-length object;
   a move mechanism for moving the long-length object relative to the light source and the long-length object relatively in the length direction of the long-length object;
   an image taking device capable of taking images of a lighted line, formed on the outer surface of the long-length object by irradiated slit light, from a direction forming an angle relative to a face of the slit light every predetermined timing;
   a position data extracting means for extracting respective height direction position data of the lighted line, which corresponds to a plurality of width direction positions of the long-length object, with respect to every taken image taken by the image taking device;
   a subtracting means for subtracting base data, which are provided to each of the width direction positions according to a shape of the outer surface of the long-length object, from each of the height direction position data, which correspond to each of the width direction positions;
   an inspection image making means for making an inspection image by arranging subtracted height direction position data of each taken image in image-taking order so as to conform to a predetermined color standard;
   a judging means for judging existence of unusual on the inspection image on the basis of a predetermined judging standard; and
   a guide mechanism for guiding the long-length object at a position which is upstream side of the moving direction of the long-length object relative to said lighted line,
   wherein the guide mechanism has a plurality of guide members which are arranged with intervals in the circumferential direction of the long-length object and each of the guide members is provided so as to be pushed on the outer surface of the long-length object.

7. The apparatus for inspecting appearance of a long-length object according to claim 6, further comprising:
   an brightness data extracting means for extracting a plurality of brightness data of the lighted line from each taken image respectively so that each brightness datum corresponds respectively to a plurality of width direction positions of the long-length object;
   a making brightness inspection image means for making a brightness inspection image by arranging said brightness data of said taken images conforming to the order of taking images so as to conform to a predetermined color standard;
   a judging means for judging existence of unusual on the brightness inspection image based on a predetermined judging standard.

8. The apparatus for inspecting appearance of a long-length object according to claim 6, further comprising:
- a plurality of guide members provided adjacent to an image taken position by the image taking device, the guide members provided mutually at intervals in the circumferential direction of the long-length object, the guide members contacting respectively to the outer surface of the long-length object, wherein
- a contact surface, which contacts to the long-length object, of each guide member is formed so as to be longer in the length direction of the long-length object than twice a pitch, in the axial direction of the long-length object, of a spiral concave portion or a spiral convex portion provided on the outer surface of the long-length object, and the contact surface is made of a material having a friction coefficient less than 0.12 relative to the outer surface of the long-length object.

9. The apparatus for inspecting appearance of a long-length object according to claim 8, further comprising:
- a pushing mechanism for pushing the guide members toward the outer surface of the long-length object with a predetermined pushing force.

10. The apparatus for inspecting appearance of a long-length object according to claim 6, wherein
- two or more light sources are provided mutually at intervals in the circumferential direction of the long-length object,
- two or more image taking devices are provided mutually at intervals in the circumferential direction of the long-length object, each image taking device is disposed at the center position relative to any two of the light sources mutually adjoining in the circumferential direction of the long-length object.

11. The apparatus for inspecting appearance of a long-length object according to claim 10, wherein
- the image taking devices and the light sources are arranged alternately in the circumferential direction of the long-length object.

12. The apparatus for inspecting appearance of a long-length object according to claim 6, further comprising:
- a making base data means for making the base data by averaging the height direction position data of a certain taken image, which are objects of subtracting, and a predetermined image-taking number of height direction position data, which are taken near the image-taking of said height direction position data and are not done by subtracting, for every width direction position.

13. The apparatus for inspecting appearance of a long-length object according to claim 6, further comprising:
- a making base data means for making the base data by averaging the height direction position data of a certain taken image, which are objects of subtracting, and a predetermined image-taking number of height direction position data, which are used in same inspection image with said height direction position data and are not done by subtracting, for every width direction position.

14. The apparatus for inspecting appearance of a long-length object according to claim 6, further comprising:
- a making base data means for providing the base data corresponding respectively to said each taken images, wherein
- the making base data means averages a predetermined image-taking number of height direction position data including the height direction position data of a certain taken image, which are objects of subtracting and taken at the center of the image-taking order of said predetermined image-taking number of height direction position data, for every width direction position.

\* \* \* \* \*